United States Patent [19]
Matsutani et al.

[11] Patent Number: 6,103,231
[45] Date of Patent: *Aug. 15, 2000

[54] ANTIBIOTIC STALOBACINS

[75] Inventors: Shigeru Matsutani, Wakayama-ken; Tadashi Yoshida, Osaka-fu; Ryuji Sakazaki, Nara-ken; Koichi Matsumoto, Osaka-fu; Shigeo Yagi, Osaka-fu; Bunji Kageyama, Osaka-fu; Yoshimi Kawamura, Osaka-fu; Toshiyuki Kamigauchi, Osaka-fu; Susumu Kamata, Osaka-fu, all of Japan

[73] Assignee: Shionogi & Co., Ltd., Osaka, Japan

[*] Notice: This patent is subject to a terminal disclaimer.

[21] Appl. No.: 08/890,756

[22] Filed: Dec. 9, 1997

Related U.S. Application Data

[63] Continuation-in-part of application No. 08/544,642, Oct. 18, 1995, which is a continuation-in-part of application No. 08/383,095, Feb. 3, 1995, abandoned, which is a division of application No. 08/243,780, May 17, 1994, Pat. No. 5,456,910, which is a continuation-in-part of application No. 08/111,045, Aug. 24, 1993, abandoned.

[51] Int. Cl.$^7$ ................................ A61K 35/74; C12P 1/04
[52] U.S. Cl. ............................................ 424/118; 435/170
[58] Field of Search .............................. 514/118; 435/170

[56] References Cited

FOREIGN PATENT DOCUMENTS 0 413 967A1   2/1991   European Pat. Off. .

OTHER PUBLICATIONS

Patent Abstracts of Japan, No. 2–303496, unexamined application, C Field, vol. 15, No. 80, Feb. 25, 1991.

Chemical Abstracts, 114: 162435V (1991).

*Primary Examiner*—Jerome D. Goldberg
*Attorney, Agent, or Firm*—Wenderoth, Lind & Ponack, L.L.P.

[57] ABSTRACT

Novel antibiotic stalobacins H-1 and I-1 having physicochemical properties as shown in Table 4 are provided, which are excellent antibiotics showing marked effects on Gram-positive bacteria.

3 Claims, 17 Drawing Sheets

ANTIBIOTIC STALOBACINS

This application is a continuation-in-part of application Ser. No. 08/544,642 filed Oct. 18, 1995, which was a continuation-in-part of now abandoned application Ser. No. 08/383,095 filed Feb. 3, 1995, which was a divisional application of Ser. No. 08/243,780 filed May 17, 1994, now issued as U.S. Pat. No. 5,456,910, which was a continuation-in-part of now abandoned application Ser. No. 08/111,045, filed Aug. 24, 1993.

The present invention relates to novel antibiotics. In particular, this invention relates to antibiotic stalobacins A, B, C, D, E, F and G produced by Pseudomonas sp. PBJ-5, 360. In addition, this invention relates to antibiotic stalobacins H-1 and I-1 produced by Pseudomonas sp. PBJ-5360-STR-1-21. Furthermore, the invention relates to the microorganisms which produce the antibiotics, and a process for producing the same.

It is well known that antibacterial activity of a particular antibiotic varies depending on a nature of bacteria to be treated and the effect of the antibiotic often reduces because of the advent of resistant strains. The advent of multiple drug resistant bacteria has recently become a big problem. Accordingly, development of novel and effective antibiotics has been desired for performing effective treatments. Above all, may Gram-positive bacteria, such as Staphylococcus, hemolytic *streptococcus* or the like are resistant to antibiotics, and there is continuous need for the development of novel antibiotics having high potency to these Gram-positive bacteria.

It is disclosed in Japanese Patent Publication (Kokai) No. 303496/1990 that Pseudomonas sp. PBJ-5,360 produces a complex of several antibiotics which is therapeutically effective on Gram-positive bacteria. However, the publication does not disclose each of the components constituting said complex. The inventors of the present invention have succeeded in isolating each of the components and determining physico-chemical property of each component. The present invention is based on such findings.

Thus, the present invention provides antibiotic stalobacins selected from the group consisting of stalobacins A, B, C, D, E, F and G produced by Pseudomonas sp. PBJ-5,360. These antibiotics are peptide antibiotics which are produced by said Pseudomonas sp. PBJ-5,360. Stalobacins A–G (hereinafter sometimes referred to as merely "stalobacins") are produced in the form of a mixture of closely related analogs by cultivating said strain of Pseudomonas. Their antibacterial activities are much more potent than those of known antibiotics. Stalobacins A–G have physico-chemical properties as shown below in Tables 1–3.

The present invention further provides antibiotic stalobacins selected from the group consisting of antibiotic stalobacins H-1 and I-1 produced by the above-noted Pseudomonas sp. PBJ-5360-STR-1-21, a variant of Pseudomonas sp. PBJ-5360. These antibiotics are peptide antibiotics which are produced by said Pseudomonas sp. PBJ-5360-STR-1-21. Stalobacins H-1 and I-1 (hereinafter sometimes also referred to as merely "stalobacins") are obtained in the form of a mixture of closely related analogs by cultivating said Pseudomonas. Their antibacterial activities are much more potent than those of known antibiotics. Stalobacins H-1 and I-1 have physico-chemical properties as shown in the following Table 4.

TABLE 1

Physico-chemical Properties of Stalobacins A and B

| | Stalobacin A | Stalobacin B |
|---|---|---|
| m.p. (° C.) (as Na salt) | 240° C. (dec.) | 240° C. (dec.) |
| LSI-MS Maximal Peak (m/z) | 1483 | 1364 |
| HRLSI-MS (MH+) (m/z) | 1483.7347 $C_{61}H_{107}N_{14}O_{28}$ | 1364.7165 $C_{58}H_{102}N_{13}O_{24}$ |
| Theoretical Value | 1483.7372 | 1364.7154 |
| IR (KBr) (cm$^{-1}$) | 3385, 1748 1653, 1526 | 3389, 1748 1653, 1526 |
| UV (H$_2$O) ($\epsilon$) at 210 nm | Terminal Absorption 36,300 | Terminal Absorption 35,500 |
| CD | $[\theta]_{196}$ − 77020 $[\theta]_{212}$ + 3159 $[\theta]_{231}$ − 33480 $[\theta]_{257}$ + 4028 | $[\theta]_{193}$ − 70720 $[\theta]_{209}$ + 17630 $[\theta]_{231}$ − 29070 $[\theta]_{257}$ + 4905 |
| Retention Time (min.) in HPLC* | 7.8 | 8.4 |
| Amino Acid Analysis (molar ratio) | | |
| HyAsp[1] | HyAsp(1) | HyAsp(1) |
| Asp | Asp(1) | Asp(1) |
| Ser | Ser(2) | Ser(1) |
| HyIle[2] | HyIle(1) | HyIle(1) |
| Gly | Gly(1) | Gly(1) |
| Ala | Ala(1) | Ala(1) |
| Arg | — | Arg(1) |
| | DNP — derivative m.p. >230° C. (dec.) HRLSI-MS 1649.7378 $C_{67}H_{109}N_{16}O_{32}$ Theoretical Value 1649.7386 | DNP — derivative m.p. >230° C. (dec.) HRLSI-MS 1530.7169 $C_{64}H_{104}N_{15}O_{28}$ Theoretical Value 1530.7169 |

*Column: Develosil 5C$_{18}$, 4.6φ × 250 mm;
Mobile Phase: CH$_3$CN/2 mM H$_3$PO$_4$ (containing 50 mM-Na$_2$SO$_4$) = 43/57;
Flow Rate: 1 ml/min.;
Chart Speed: 1 cm/min.
[1]Hydroxyaspartic acid
[2]Hydroxyisoleucine

TABLE 2

Physico-chemical Properties of Stalobacins C and D

| | Stalobacin C | Stalobacin D |
|---|---|---|
| LSI-MS Maximal Peak (m/z) | 1396 | 1309 |
| HRLSI-MS (MH+) (m/z) | 1396.7061 $C_{58}H_{102}N_{13}O_{26}$ | 1309.6706 $C_{55}H_{97}N_{12}O_{24}$ |
| Theoretical Value | 1396.7053 | 1309.6732 |
| IR (KBr) (cm$^{-1}$) | 3411, 1744 1652, 1528 | 3418, 1745 1646, 1525 |
| UV (H$_2$O) | Terminal Absorption | Terminal Absorption |
| Retention Time (min.) in HPLC* | 8.8 | 10.0 |
| Amino Acid Analysis (molar ratio) | | |
| HyAsp[1] | HyAsp(1) | HyAsp(1) |
| Asp | Asp(1) | Asp(1) |
| Ser | Ser(1) | — |
| HyIle[2] | HyIle(1) | HyIle(1) |
| Gly | Gly(1) | Gly(1) |
| Ala | Ala(1) | Ala(1) |
| Arg | — | — |

*Column: Develosil 5C$_{18}$, 4.6φ × 250 mm;
Mobile Phase: CH$_3$CN/2 mM H$_3$PO$_4$ (containing 50 mM-Na$_2$SO$_4$) = 43/57;
Flow Rate: 1 ml/min.;
Chart Speed: 1 cm/min.
[1]Hydroxyaspartic acid
[2]Hydroxyisoleucine

TABLE 3

Physico-chemical Properties of Stalobacins E, F and G

|  | Stalobacin E | Stalobacin F | Stalobacin G |
|---|---|---|---|
| m.p. (° C.) (as Na salt) | 240° C. dec. | 240° C. dec. | 240° C. dec. |
| LSI-MS Maximal Peak (m/z) | 1378 | 1497 | 1485 |
| HRLSI-MS (MH$^+$) (m/z) | 1378.7318 | 1497.7532 | 1485.7529 |
|  | $C_{59}H_{104}N_{13}O_{24}$ | $C_{62}H_{109}N_{14}O_{28}$ | $C_{61}H_{109}N_{14}O_{28}$ |
| Theoretical Value | 1378.7311 | 1497.7529 | 1485.7529 |
| IR (KBr) (cm$^{-1}$) | 3418, 1748 | 3369, 1746 | 3369, 1746 |
|  | 1651, 1526 | 1653, 1527 | 1654, 1528 |
| UV) (H$_2$O) | Terminal Absorption | Terminal Absorption | Terminal Absorption |
| ($\epsilon$) at 210 nm | 39,500 | 36,480 | 37,500 |
| CD | $[\theta]_{194} - 53530$ | $[\theta]_{196} - 80050$ | $[\theta]_{196} - 58600$ |
|  | $[\theta]_{208} + 15380$ | $[\theta]_{212} + 1022$ | $[\theta]_{212} + 10060$ |
|  | $[\theta]_{231} - 26750$ | $[\theta]_{231} - 34490$ | $[\theta]_{231} - 49830$ |
|  | $[\theta]_{256} + 4512$ | $[\theta]_{257} + 4788$ | $[\theta]_{257} + 5621$ |
| Retention Time (min.)* in HPLC | 12.4 | 11.7 | 17.0 |
| Amino Acid Analysis (Molar Ratio) |  |  |  |
| HyAsp[1] |  | HyAsp(1) | HyAsp(1) | HyAsp(1) |
| Asp |  | Asp(1) | Asp(1) | Asp(1) |
| Ser |  | Ser(1) | Ser(2) | Ser(2) |
| HyIle[2] |  | HyIle(1) | HyIle(1) | HyIle(1) |
| Gly |  | Gly(1) | Gly(1) | Gly(1) |
| Ala |  | Ala(1) | Ala(1) | Ala(1) |
| Arg |  | Arg(1) | — | — |

*Column: Develosil 5C$_{18}$, 4.6$\phi$ × 250 mm;
Mobile Phase: CH$_3$CN/2 mM H$_3$PO$_4$ (containing 50 mM-Na$_2$SO$_4$) = 43/57;
Flow Rate: 1 ml/min.;
Chart Speed: 1 cm/min.
[1] Hydroxyaspartic acid
[2] Hydroxyisoleucine

TABLE 4

Physico-chemical Properties of Stalobacins H-1 and I-1

|  | Stalobacin H-1 | Stalobacin I-1 |
|---|---|---|
| m.p. (° C.) (as Na salt) | 235° C. (dec.) | 240° C. (dec.) |
| LSI-MS Maximal Peak (m/z) | 1396 | 1325 |
| HRLSI-MS (MH$^+$) (m/z) | 1396.6985 | 1325.6583 |
|  | $C_{60}H_{97}N_{15}O_{23}$ | $C_{57}H_{92}N_{14}O_{22}$ |
| Theoretical value | 1396.6954 | 1325.6583 |
| IR (KBr) (cm$^{-1}$) | 3374, 1747, | 3387, 1747, |
|  | 1654, 1597, 1525 | 1651, 1596, 1527 |
| UV (H$_2$O) | Terminal absorption | Terminal absorption |
| CD (H$_2$O) | $[\theta]_{194} - 66980$ |  |
|  |  | $[\theta]_{206} + 11530$ |
|  | $[\theta]_{212} + 9851$ |  |
|  |  | $[\theta]_{232} - 28660$ |
|  | $[\theta]_{232} - 31520$ |  |
|  |  | $[\theta]_{257} + 4749$ |
|  | $[\theta]_{257} + 4288$ |  |
| Retention time (min.) in HPLC* | 8.8 | 9.7 |
| Amino Acid Analysis (molar ratio) |  |  |
| HyAsp[1] | HyAsp(1) | HyAsp(1) |
| Asp | Asp(1) | Asp(1) |
| Ser | Ser(1) | Ser(1) |
| HyIle[2] | HyIle(1) | HyIle(1) |
| Gly | Gly(1) | Gly(1) |
| Ala | Ala(1) | — |

*Column: Develosil 5C18, 4.6 i.d. × 250 mm
Mobile phase: CH$_3$CN/2 mM H$_3$PO$_4$ (containing 50 mM Na$_2$SO$_4$) = 43/57
Flow rate: 1 ml/min.

TABLE 4-continued

Physico-chemical Properties of Stalobacins H-1 and I-1

[1] Hydroxyaspartic acid
[2] Hydroxyisoleucine

The antibiotic stalobacins of the present invention characterized by the above properties have been found to have excellent antibacterial activities in vitro and in vivo, showing potent effects especially on Gram-positive bacteria.

Thus, the antibiotic stalobacins of the present invention show excellent activities, and have higher activities especially against Gram-positive bacteria, as shown below in Tables 7 and 9. Regarding stalobacins A–G, the mechanism is considered to be based on the inhibition of cell wall synthesis.

No death was observed in acute toxicity test by intravenous administration of 300 mg/kg and 500 mg/kg of the antibiotic stalobacins to mice.

The antibiotic stalobacins A–G of the present invention are produced by cultivating Pseudomonas sp. PBJ-5,360 belonging to Genus Pseudomonas aerobically in liquid medium containing assimilable carbon sources, nitrogen sources and mineral salts in a conventional manner. This bacterium has been identified as the above-mentioned strain by cultivating it according to the method as hereinafter described in Experiment 2 and examining comprehensively its morphology, culture properties, physiological and biochemical properties in reference to the description of Bergy's Manual of Systematic Bacteriology, Vol. 1 (1984). This strain may undergo a spontaneous or artificial mutation, and it is obvious to a person skilled in the art that such mutants should be included in the scope of the present invention, as far as they retain an ability to produce the stalobacins of the present invention. Thus, the present invention provides also Pseudomonas sp. PBJ-5,360 producing novel antibiotic stalobacins and mutants thereof having an ability to produce said antibiotic stalobacins. Pseudomonas sp. PBJ-5,360 was deposited under accession No. FERM P-10578 with National Institute of Bioscience and Human Technology, Higashi 1-1-3, Tsukuba-shi, Ibaraki Pref. Japan, on Feb. 27, 1989, and then transferred to International Deposition under Budapest Treaty on Jun. 17, 1993, and assigned accession No. FERM BP-4342.

Antibiotic stalobacins H-1 and I-1 of the present invention are produced by cultivating Pseudomonas sp. PBJ-5360-STR-1-21, a variant derived from Pseudomonas sp. PBJ-5360 (BIKOKEN deposition No. 10578, FERM BP-4342), which produces a mixture of stalobacins, aerobically in a liquid medium containing assimilable carbon sources, nitrogen sources and mineral salts in a conventional manner. This bacterium has been identified as the above mentioned strain by cultivating it according to the method as hereinafter described in Experiment 4 and examining comprehensively its morphology, culture properties, physiological and biochemical properties in reference to the description of Bergey's Manual of Systematic Bacteriology, Vol. 1 (1984). This strain may undergo a spontaneous or artificial mutation, and it is obvious to a person skilled in the art that such mutants should be included in the scope of the present invention, as far as they retain an ability to produce the stalobacins of the present invention. Thus, the present invention provides also Pseudomonas sp. PBJ-5360-STR-1-21 producing novel antibiotic stalobacins H-1 or I-1 and mutants thereof having an ability to produce said antibiotic stalobacins. Pseudomonas sp. PBJ-5360-STR-1-21 was deposited under accession No. FERM BP-4661 with National Institute of Bioscience and Human Technology, Higashi 1-1-3, Tsukubashi, Ibaraki Pref. Japan, on Apr. 28, 1994.

Furthermore, the present invention provides a process for producing antibiotic stalobacins H-1 and I-1 by cultivating such strains.

Ordinary compositions of medium and ordinary conditions used for conventional cultivation for producing antibiotics can be adopted. In principle, the medium includes carbon sources, nitrogen sources, mineral salts and the like. If necessary, vitamins, precursors or the like can be added. Examples of carbon sources are glucose, starch, dextrin, glycerin, molasses, organic acids and the like, and these carbon sources may be used alone or in a mixture thereof. Examples of nitrogen sources are soybean powder, corn steep liquor, meat extract, yeast extract, cotton seed powder, peptone, wheat embryos, ammonium sulfate, ammonium nitrate and the like, and these nitrogen sources may be used alone or in a mixture thereof. Examples of mineral salts are calcium carbonate, sodium chloride, potassium chloride, magnesium sulfate, cupric sulfate, manganese chloride, zinc sulfate, cobalt chloride, various phosphates and the like. These mineral salts may be added to a medium when required. A sufficient amount of antibiotic stalobacins A to G is produced by cultivating Pseudomonas sp. PBJ-5,360 of the present invention in an appropriate medium at temperature from 20 to 35° C., preferably 25–29° C., for about 1–7 days. Similarly, a sufficient amount of antibiotic stalobacins H-1 and I-1 is produced by cultivating Pseudomonas sp. PBJ-5360-STR-1-21 of the present invention in an appropriate medium at temperatures from 20 to 35° C., preferably 25 to 29° C., for about 1 to 7 days. The product is then isolated and purified, if necessary, from the culture in a conventional manner. All of such procedures are well known to a person skilled in the art.

The antibiotic stalobacins of the present invention are believed to be useful for treating various infections, in particular, treating infections caused by multiple drug-resistant Gram-positive bacteria, since they exhibit marked antibacterial activities in vivo and in vitro.

Figure 1:
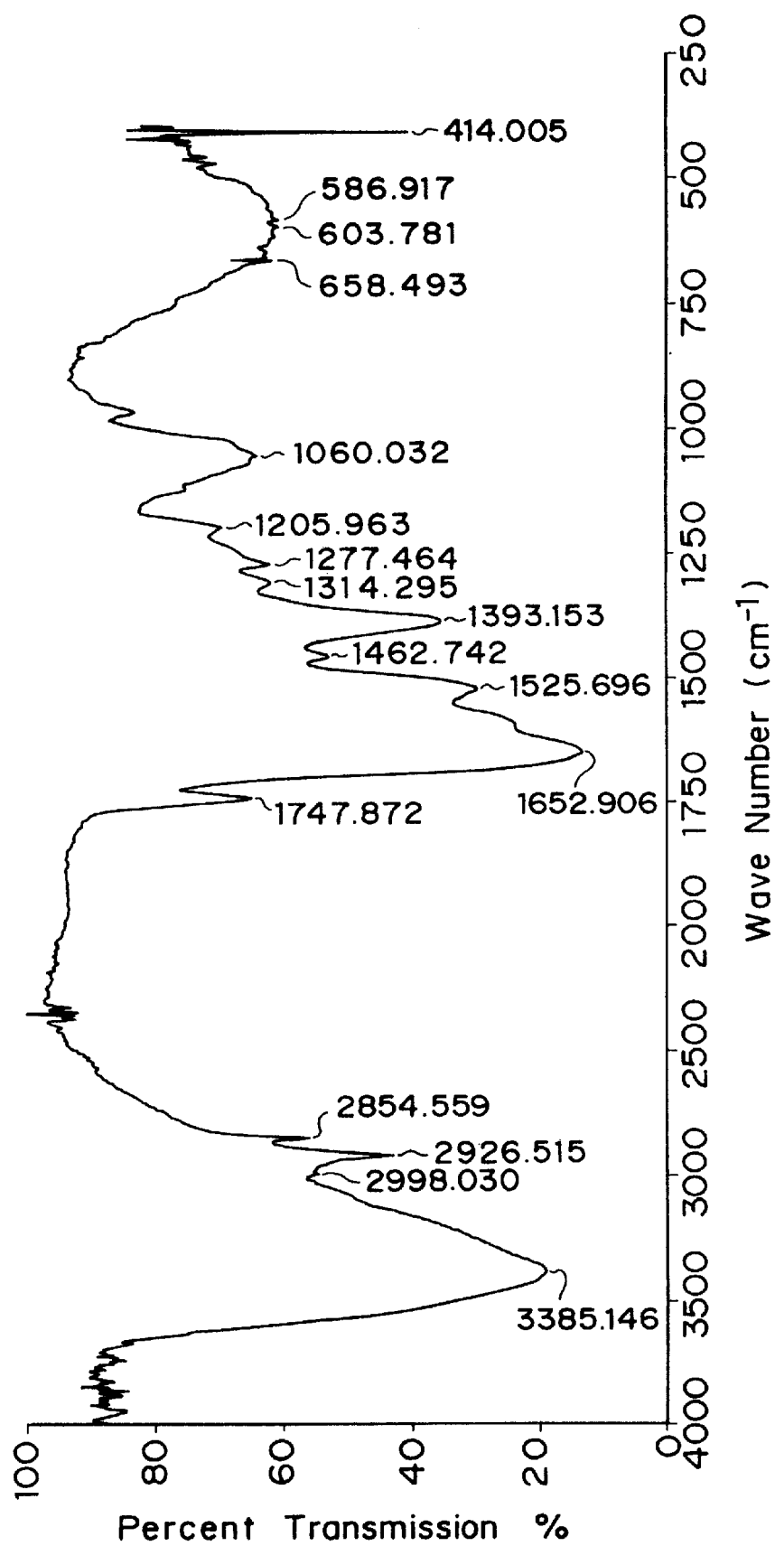
FIG. 1 shows IR spectrum of stalobacin A.
Figure 2:
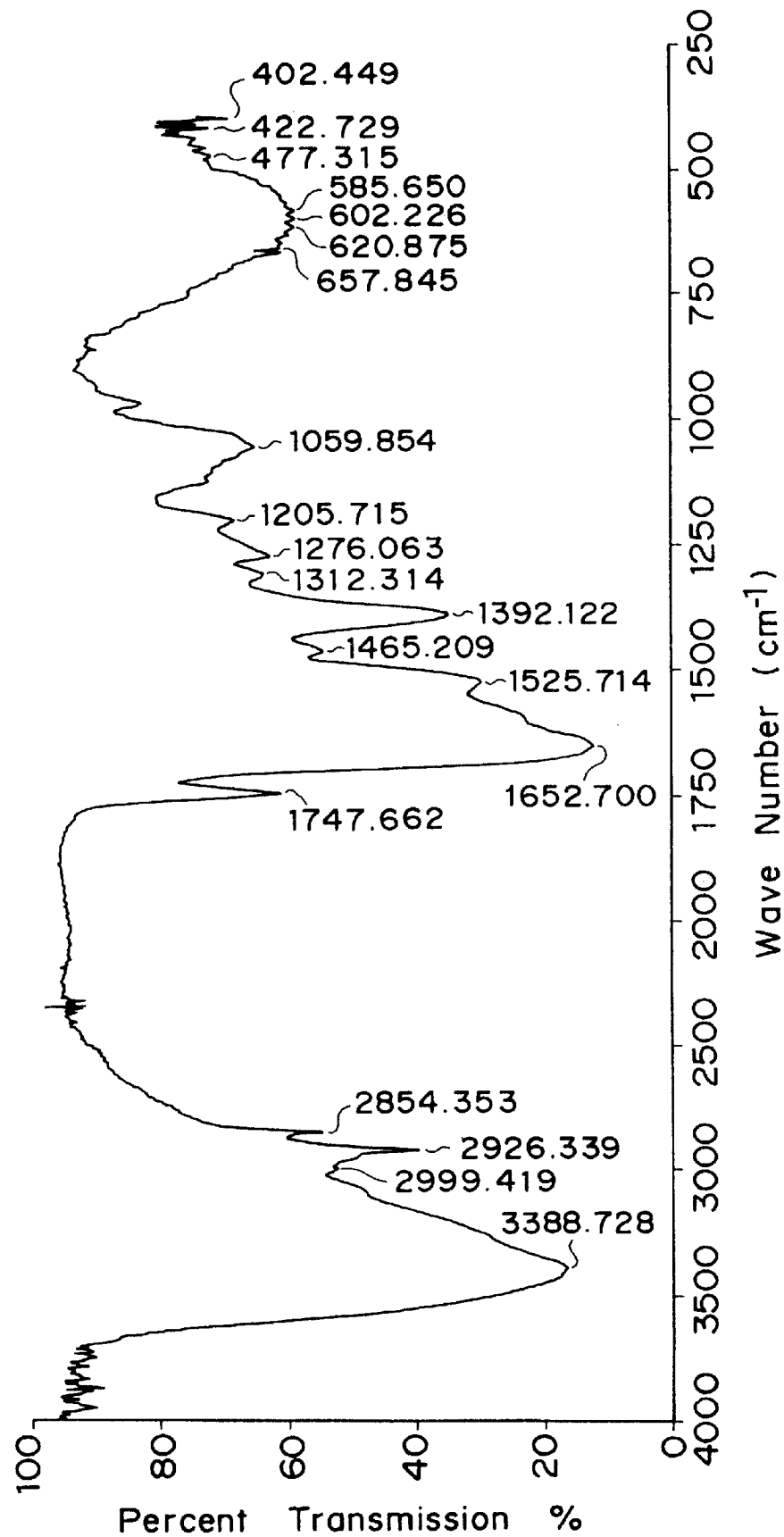
FIG. 2 shows IR spectrum of stalobacin B.
Figure 3:
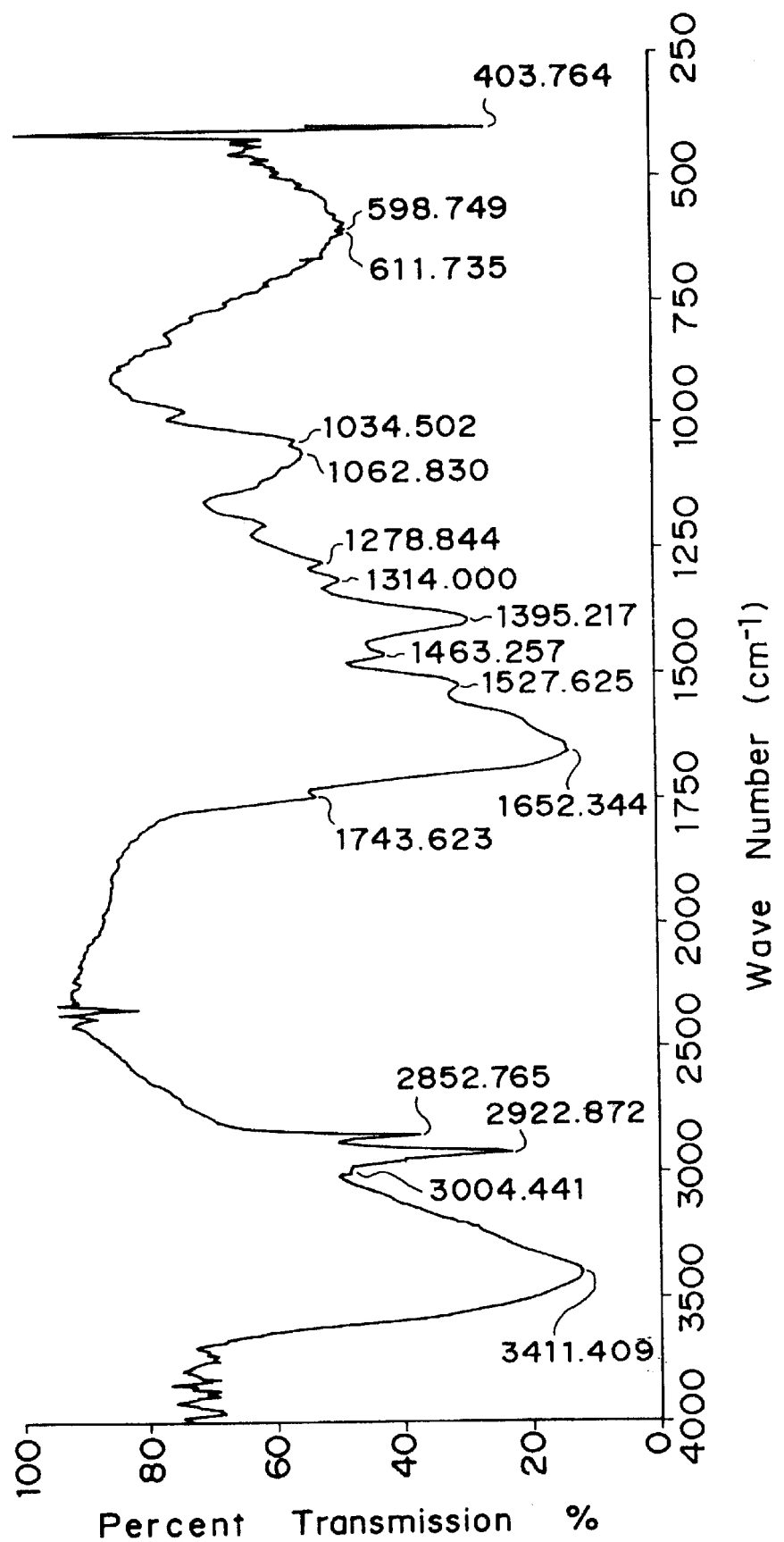
FIG. 3 shows IR spectrum of stalobacin C.
Figure 4:
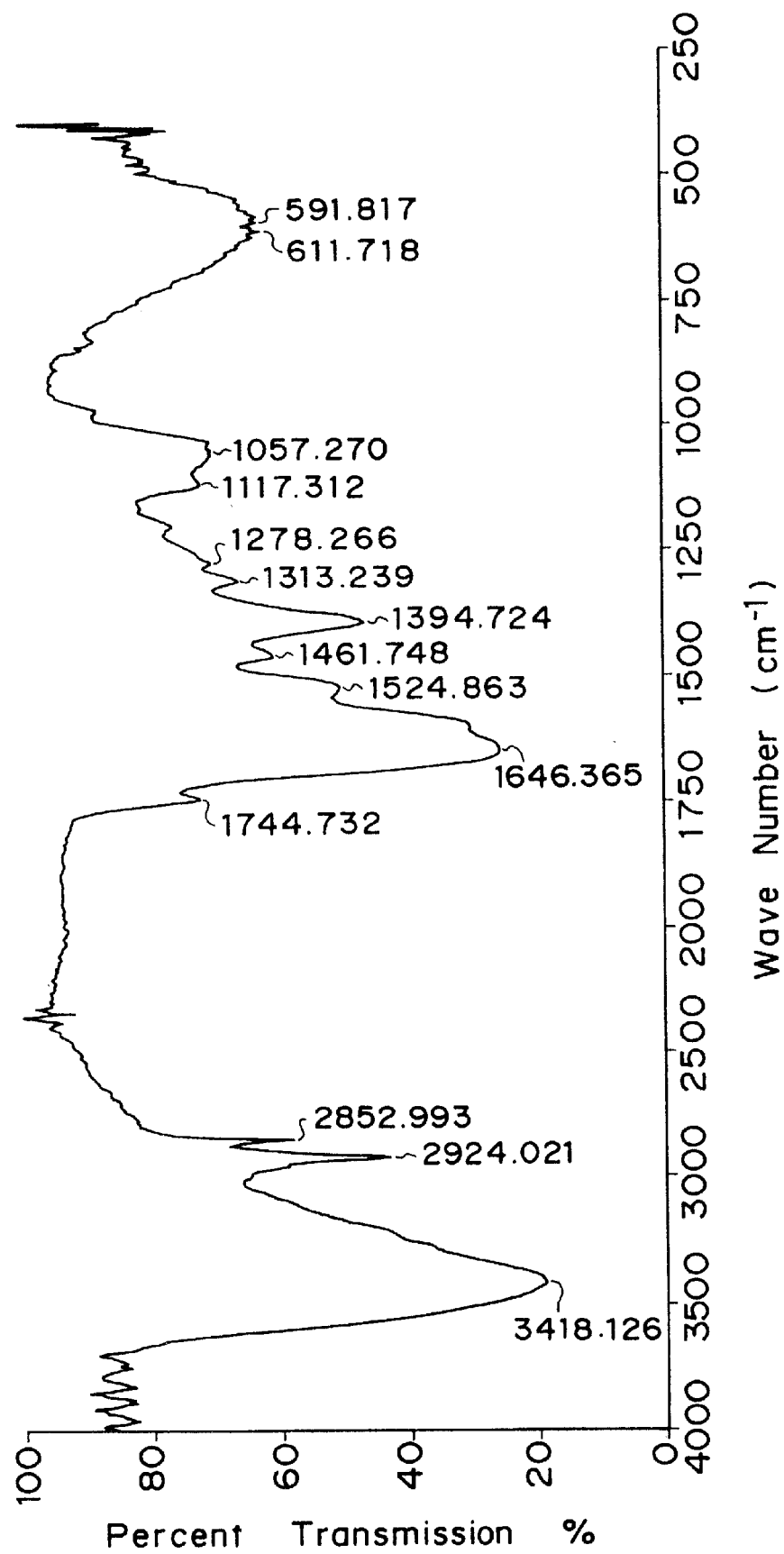
FIG. 4 shows IR spectrum of stalobacin D.
Figure 5:
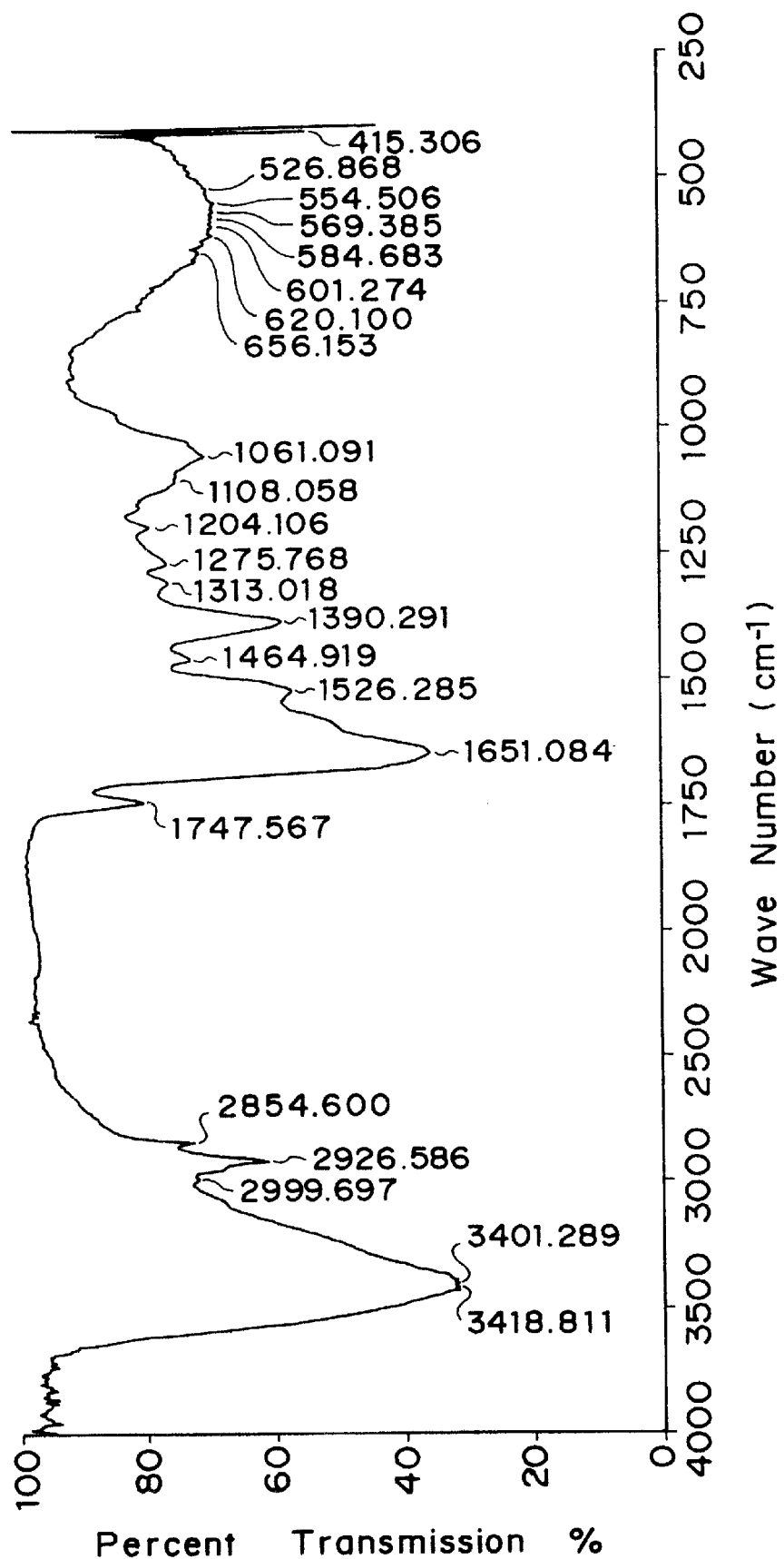
FIG. 5 shows IR spectrum of stalobacin E.
Figure 6:
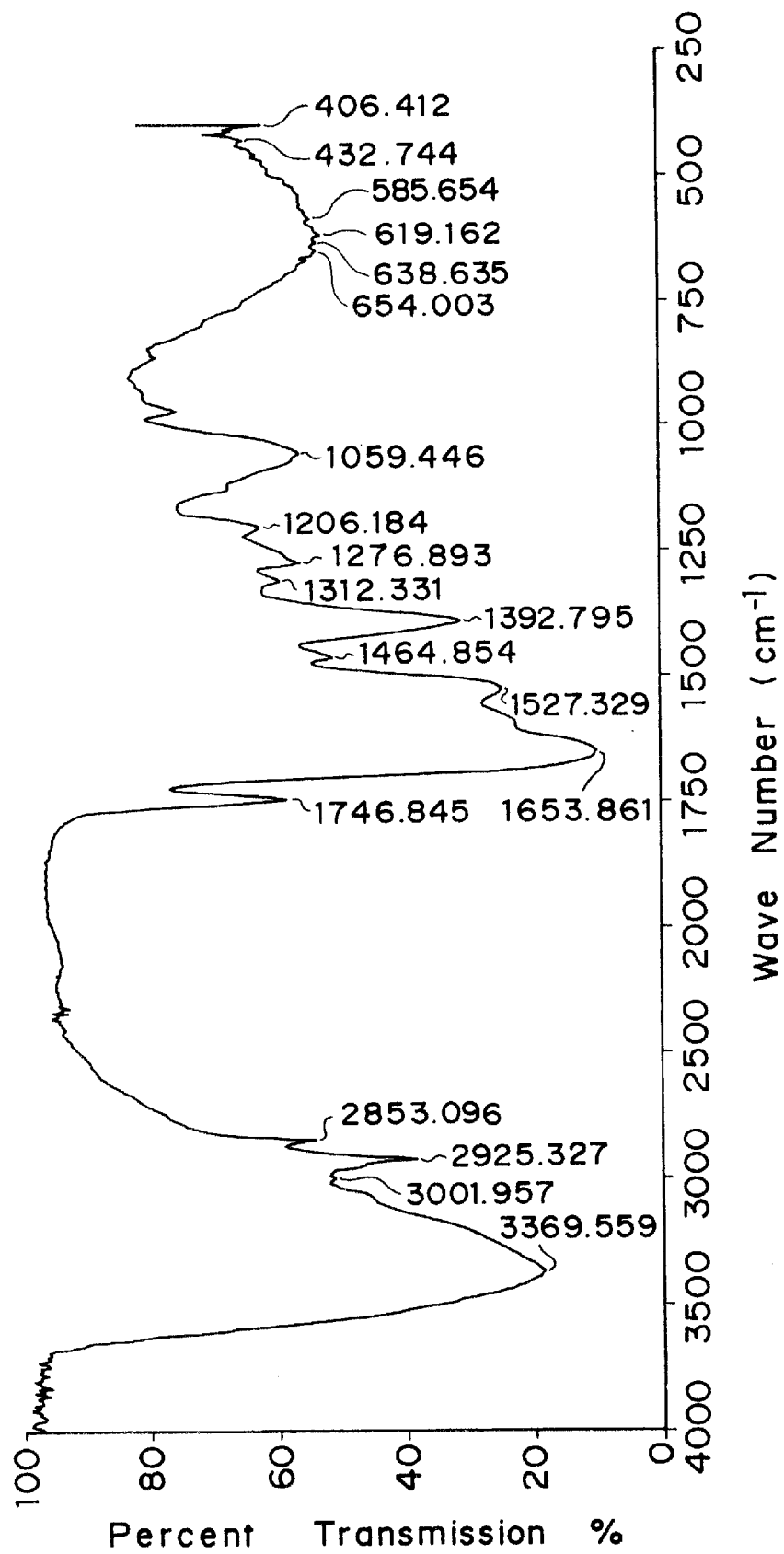
FIG. 6 shows IR spectrum of stalobacin F.
Figure 7:
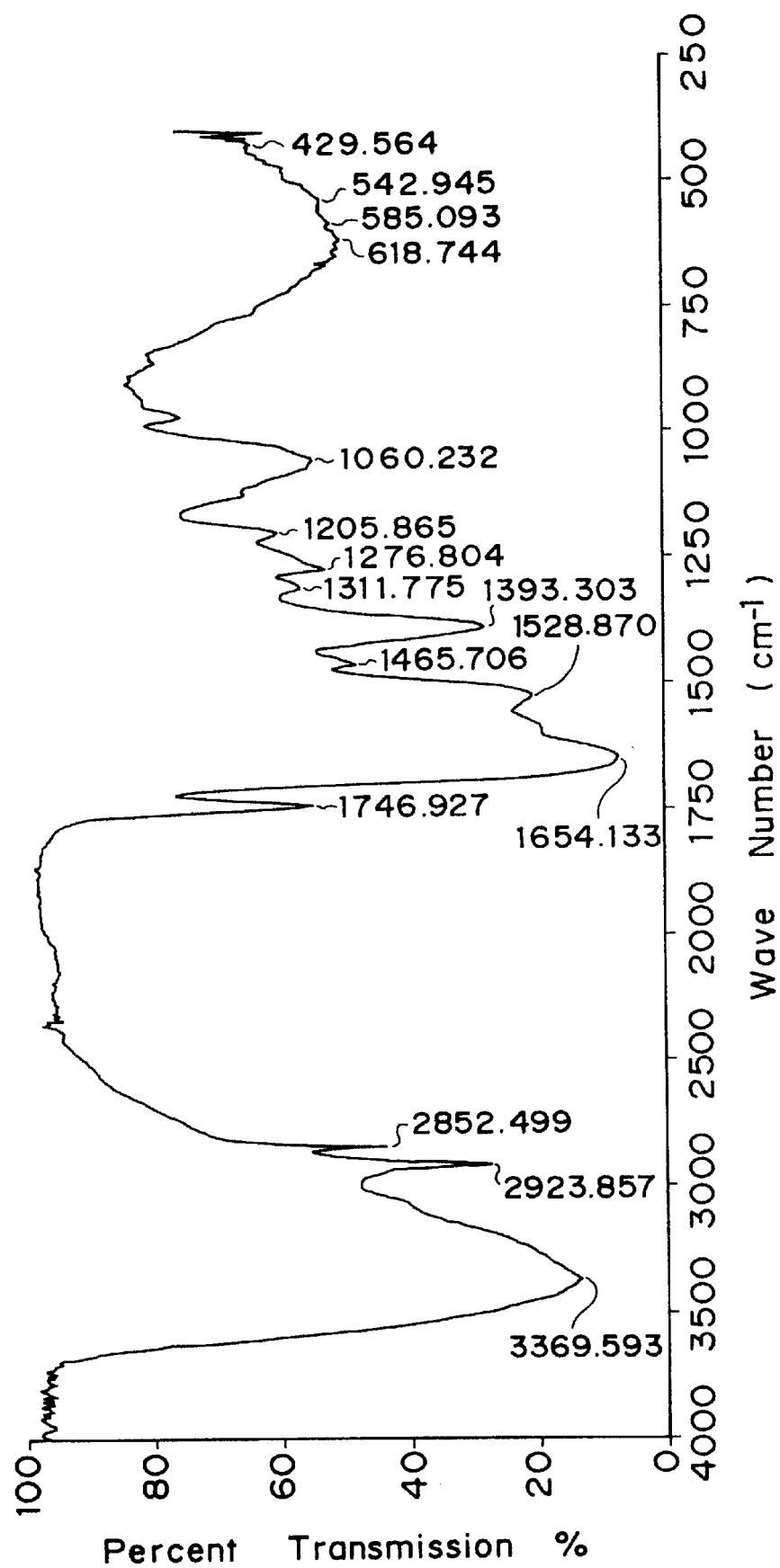
FIG. 7 shows IR spectrum of stalobacin G.
Figure 8:
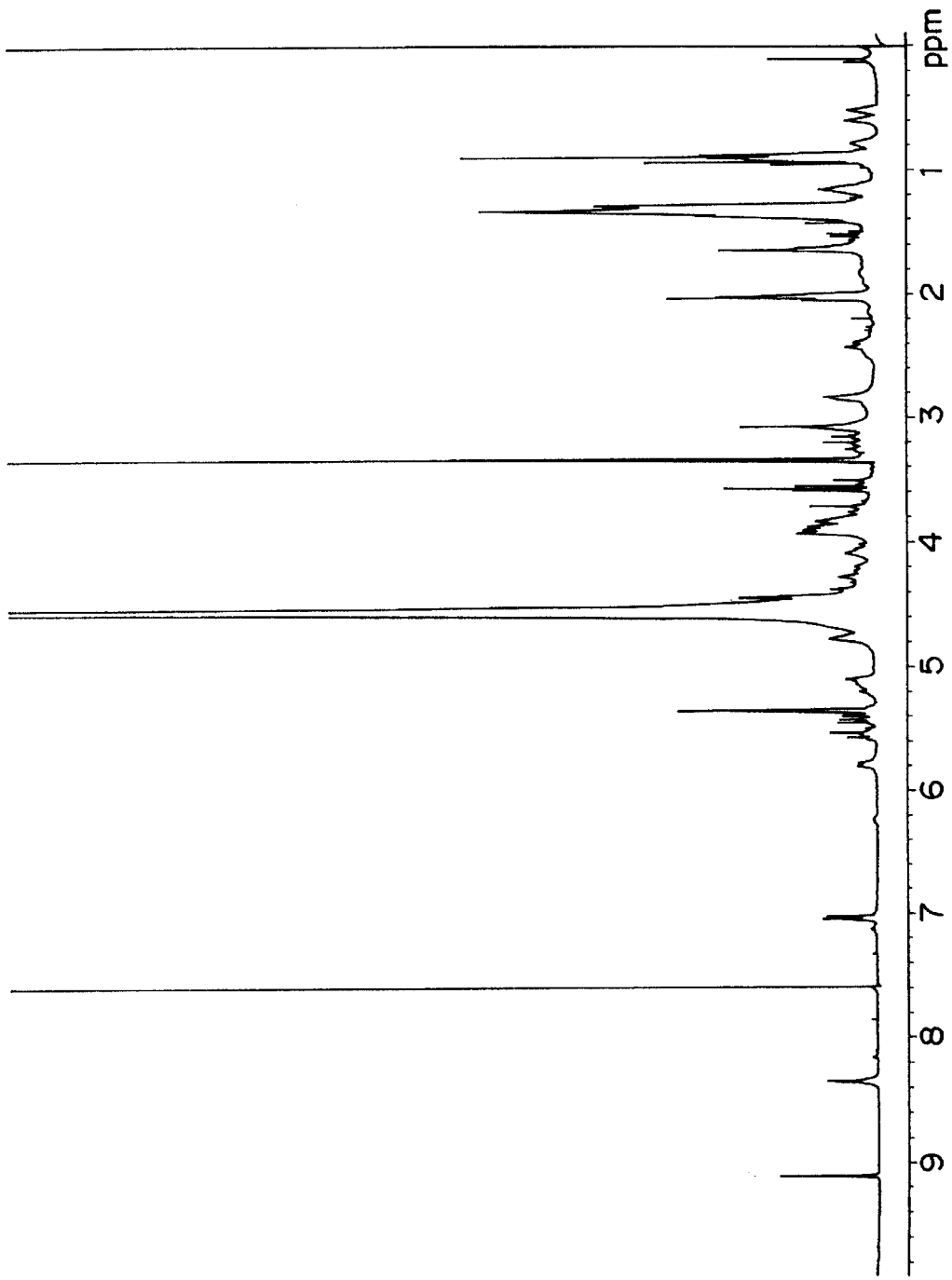
FIG. 8 shows NMR spectrum of DNP-stalobacin A.
Figure 9:
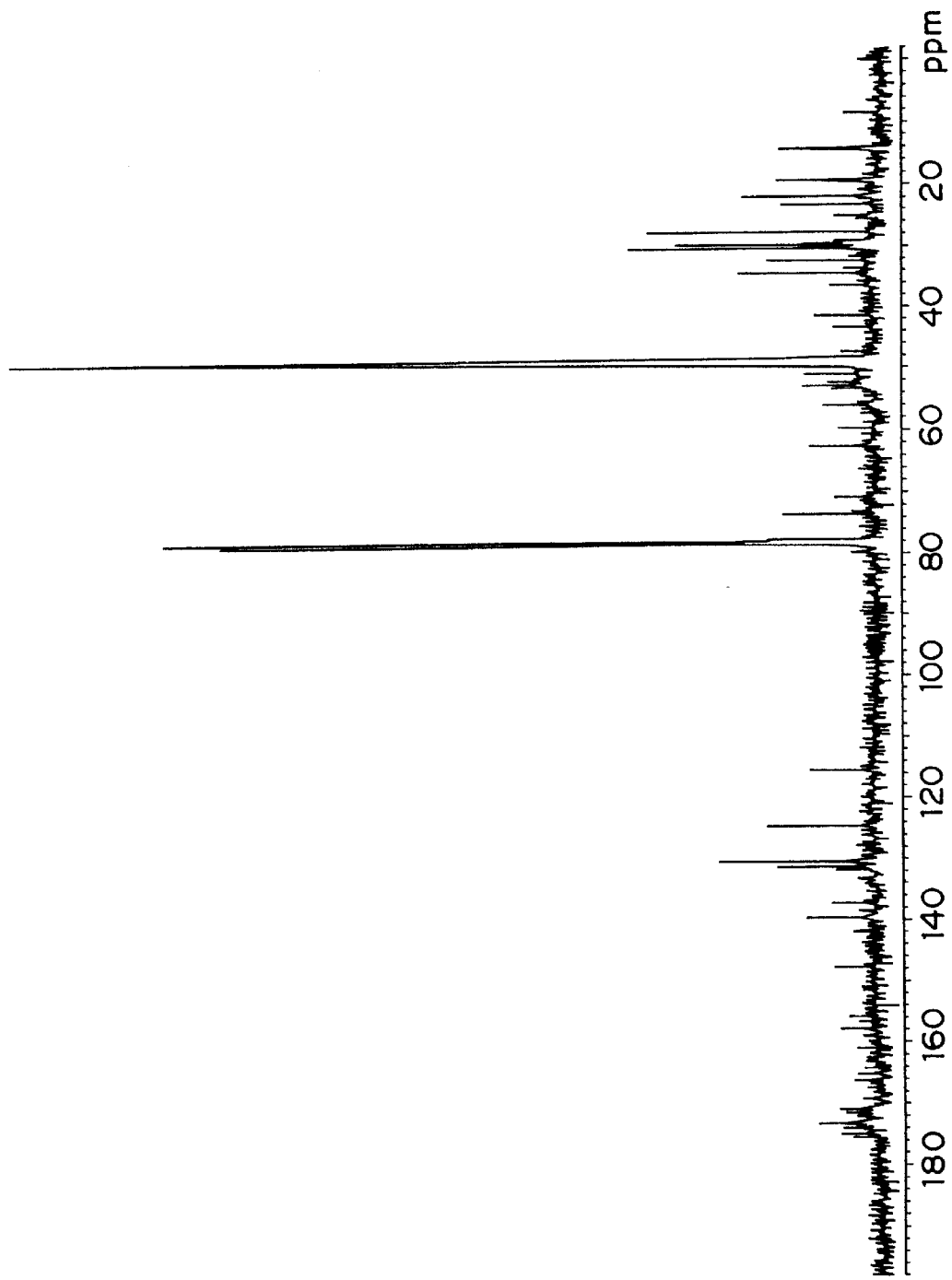
FIG. 9 shows NMR spectrum of DNP-stalobacin B.
Figure 10:
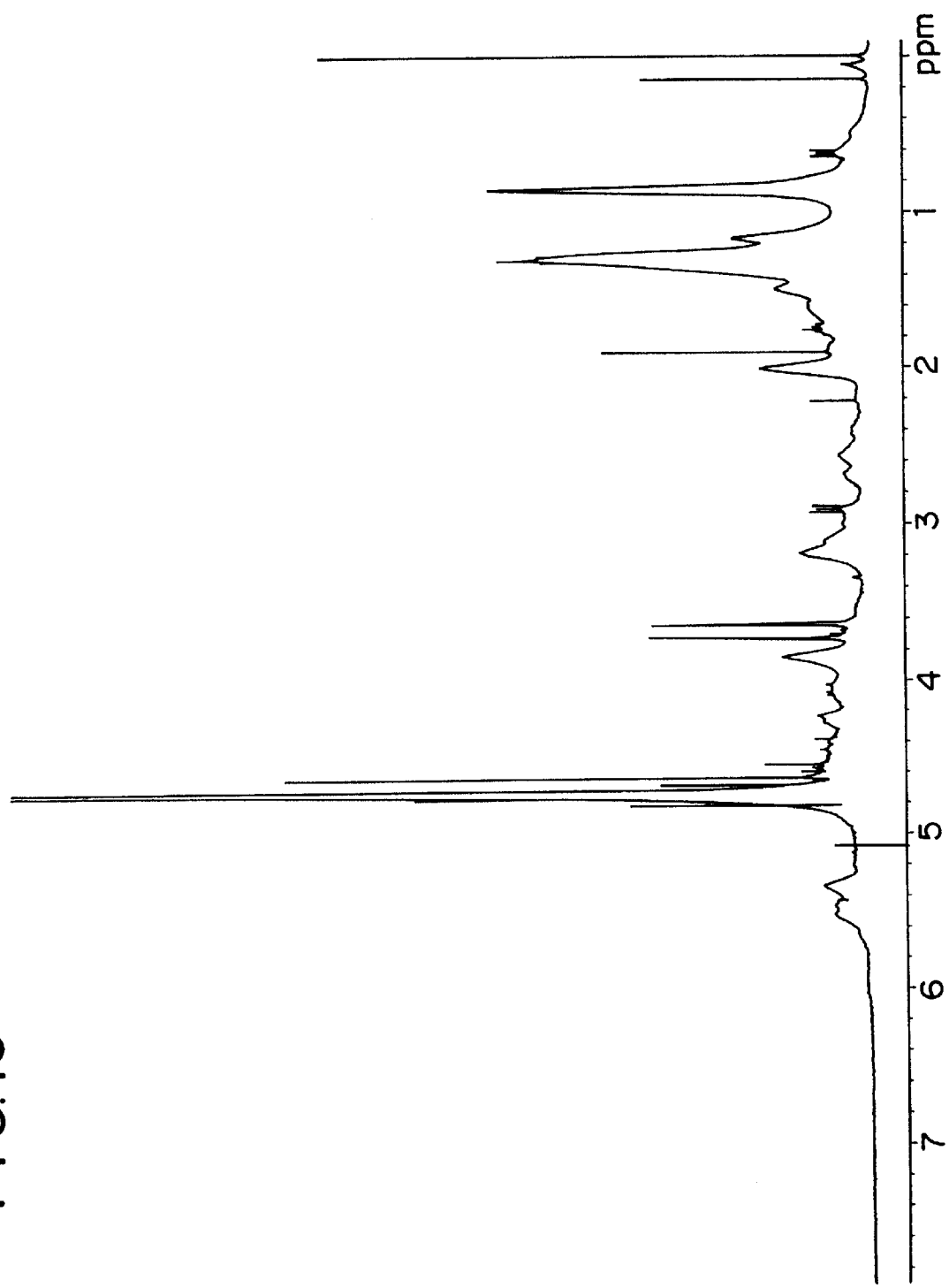
FIG. 10 shows NMR spectrum of stalobacin E.
Figure 11:
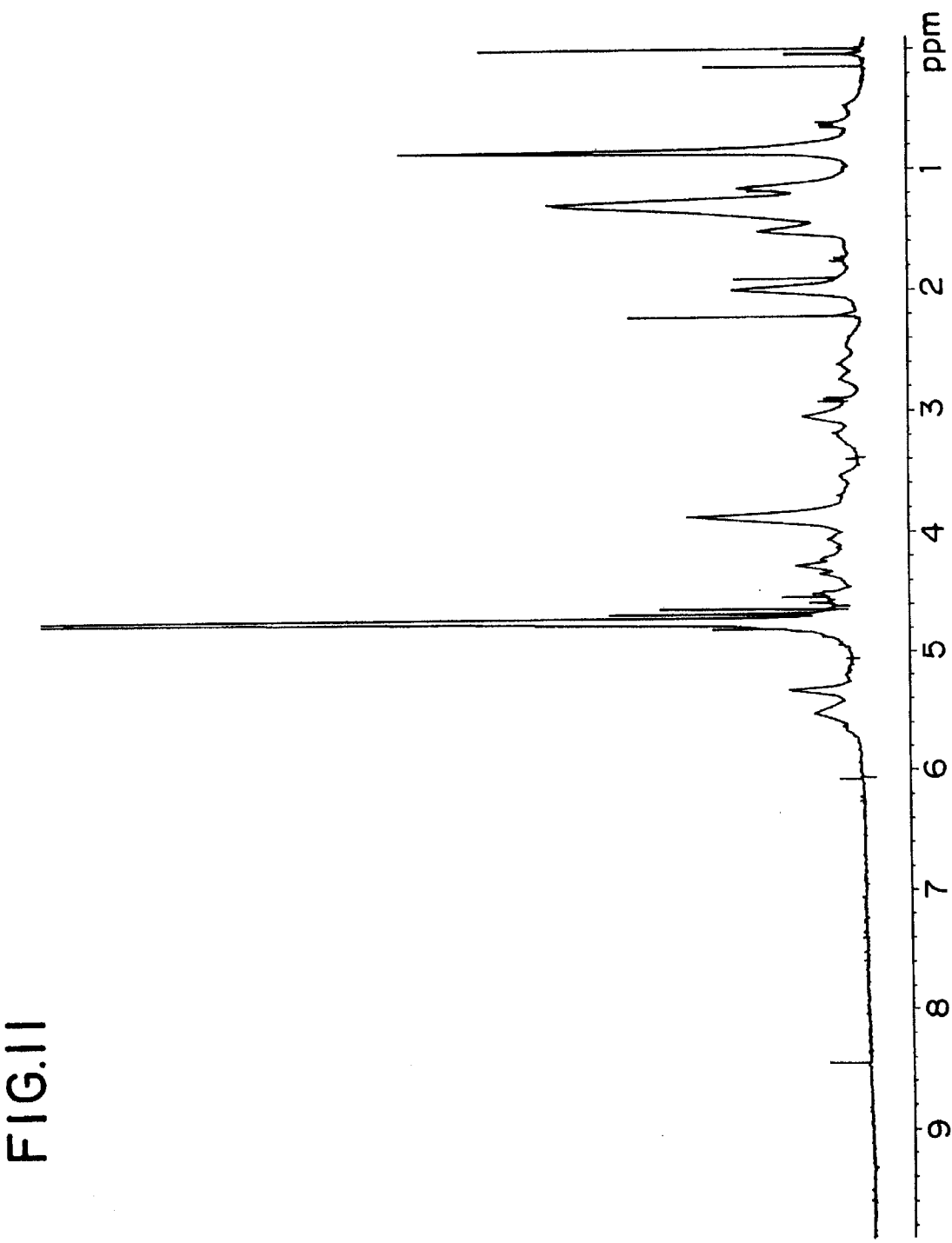
FIG. 11 shows NMR spectrum of stalobacin F.
Figure 12:
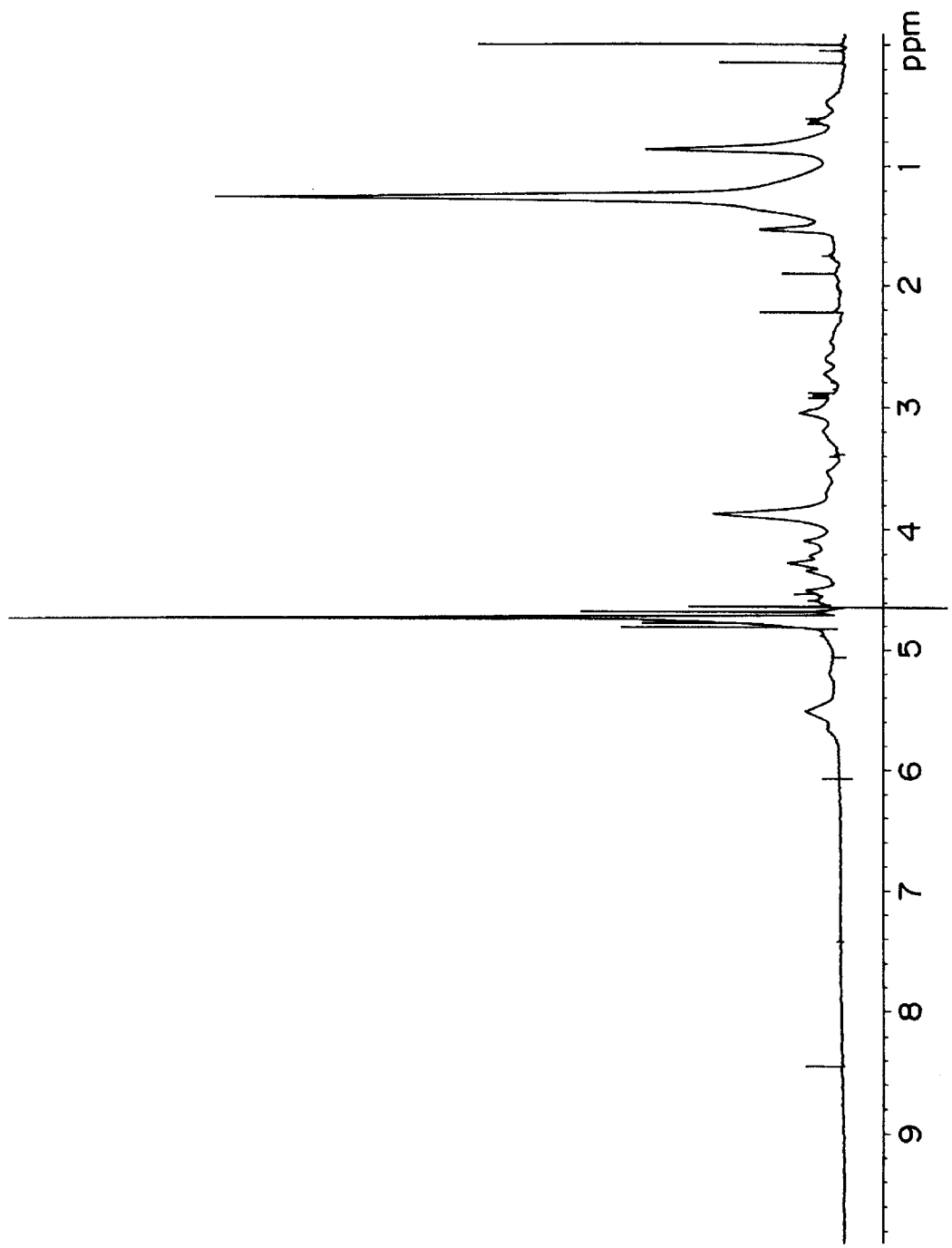
FIG. 12 shows NMR spectrum of stalobacin G.

The present invention will be explained in more detail below by illustrating Examples and Experiments.

EXAMPLE 1

(a) Fermentation Step:

Eight hundreds ml of a medium (adjusted to pH 7 with 2 N-NaOH) consisting of 1.0% glucose, 0.5% yeast extract (Difco) and tap water in a 2 L Erlenmeyer flask was inoculated with Pseudomonas sp. PBJ-5,360 (kept at −80° C. in 2 ml vial), and the resultant mixture was subjected to a shaking cultivation at 180 rpm with 70 mm of shaking breadth at temperature of 28° C. for 20 hours. The culture (800 ml) was implanted to 25 L of a medium (adjusted to pH 7 with 2 N-NaOH) containing 1.0% glucose, 0.4% yeast extract (Difco), 1.0% molt extract (Difco), 0.1% polypeptone (Nippon Seiyaku) and tap water in 50 L jar fermenter, and the resultant mixture was cultivated with agitation at 200 rpm, with 20 L/min of aeration, under 0.35 kg/cm$^2$ of inner pressure, at temperature of 28° C. for 20 hours.

Then, 13 L of this culture was implanted to 250 L of a medium (adjusted to pH 7 with 2 N-NaOH) consisting of 1.0% glucose, 1.0% molt extract (Difco), 1.0% powdery yeast, 0.2% tomato paste (Kagome), 1.0% β-cyclodextrin, 0.0008% defoaming agent P-2000 (Dainippon Ink) and tap water in a 500 L tank, and the resultant mixture was cultivated with 120 L/min of aeration, under 0.35 kg/cm$^2$ of inner pressure, with agitation at 320 rpm at a temperature of 28° C. for 94 hours.

(b) Separation Step:

To 375 L of the culture obtained in the foregoing step was added 3.7 L of chloroform for sterilization. Then, the mixture was adjusted to pH 8.5 with 2 N-NaOH, mixed with 27 L of Diaion HP-20 (Mitsubishi Kasei Corporation) and stirred for 4 hours for adsorbing the active substances onto the resin. The mixture was allowed to stand for 1 hour, and the supernatant was discarded to recover Diaion HP-20. The resin was washed with water and put in a glass column (inner diameter: 30 cm), and the active substances were eluted by a gradient of 40 L of 10 mM $Na_2HPO_4$-40 L of 90% methanol.

The fraction (21 L) showing antibacterial activity to S. aureus JC-1 was collected, adjusted to pH 7.0 with 2 N-HCl and concentrated in vacuo to 3 L. The concentrate was washed with 3 L of ethyl acetate to remove lipophilic materials. The ethyl acetate contained in the aqueous layer was evaporated in vacuo and the residue was charged onto MCI-GEL CHP 20P (Mitsubishi Kasei Corporation) column (5 cm I.D.×51 cm) to adsorb the active substances, and the active substances were eluted stepwise with 2 mM $Na_2HPO_4$-80% MeOH.2 mM $Na_2HPO_4$. The eluted fractions were subjected to a HPLC analysis, and the fractions containing a group of stalobacins were collected, adjusted to pH 7.0 with 2 N-HCl, concentrated in vacuo and lyophilized. 3490 mg.

(c) Purification Step:

The First Purification Step:

Two lots of the crude extract obtained in the foregoing step were combined and dissolved in 230 ml of water (pH 8). The solution was adsorbed on Whatman DE-52 (Cl$^-$) ion exchange cellulose column (2 cm I.D.×50 cm), and the column was washed with water. The column was subjected to a gradient elution with 600 ml of 10 mM $Na_2HPO_4$ (pH 7.5)–600 ml of 1 M NaCl·10 mM $Na_2HPO_4$ (pH 7.5). The eluted fractions were subjected to a HPLC analysis, and 370 ml of the fractions containing a group of stalobacins were collected and adjusted to pH 7.0 with 2 N-HCl. The above fraction (370 ml) was adsorbed on MCI-GEL CHP 20P (Mitsubish Kasei Corporation) column (2 cm I.D.×50 cm), which was then subjected to a gradient elution with 10 mM $Na_2HPO_4$ (pH 7.5)–90% MeOH·10 mM $Na_2HPO_4$ (pH 7.5). The eluted fractions were subjected to a HPLC analysis, and the fractions containing a group of stalobacins were collected, adjusted to pH 7.0 with 2 N-HCl, concentrated in vacuo and lyophilized.

TABLE 5

| Fraction *No. | mg | Ingredient |
| --- | --- | --- |
| 1–63 | Ca. 0 | |
| 63–75 | 1400 | Stalobacins B, E |
| 76–90 | 600 | Stalobacins A, B |
| 91–134 | 1250 | Stalobacins A, C, D, F, G |

*: 15 ml/Fraction

The Second Purification Step:

The fractions obtained above were purified by the preparative high performance liquid chromatography under the following conditions and then by the recycle preparative high performance liquid chromatography to give stalobacins A, B, C, D, E, F and G.

Fractions 63–75 (1400 mg) were dissolved in 40 ml of pure water, and the solution was subjected to the preparative high performance liquid chromatography with YMC ODS column (s-15/30μ, 5.0×5.0 cm, eluent: acetonitrile-2 mM phosphoric acid (50 mM $Na_2SO_4$) 47:53, flow rate: 100 ml/min, detection: 220 nm) to give a fraction (1.2 L) containing stalobacin B as a main ingredient and a fraction (2.0 L) containing stalobacin E as a main ingredient. Each fraction was neutralized with dilute aqueous sodium hydroxide and the acetonitrile was evaporated. The residue was adjusted to pH 7.4–7.5 and adsorbed on a column of MIC-GEL CHP-20P, which was washed with water and eluted with 60% aqueous acetone. Eluates were concentrated in vacuo and lyophilized to give 92 mg of stalobacin B fraction and 20 mg of stalobacin E fraction. The stalobacin B fraction (92 mg) obtained above was subjected to the recycle preparative high performance liquid chromatography with Develosil 5 $C_{18}$ column (2.0×25 cm, eluent: acetonitrile-2 mM phosphoric acid (50 mM $Na_2SO_4$) 47:53, flow rate: 10 ml/min., detection: 220 nm)(twice repeated). The fraction separated was concentrated to remove the acetonitrile, and the residue was neutralized with dilute sodium hydroxide, adjusted to pH 7.3–7.5, adsorbed on a column of MIC-GEL CHP-20P, which was then washed with water and eluted with 60% aqueous acetone. The eluate was concentrated in vacuo to remove the acetone, and the residue was lyophilized to give 42 mg of pure stalobacin B. Further, the stalobacin E fraction (20 mg) obtained above was subjected to the recycle preparative high performance liquid chromatography (twice repeated) using Develosil 5 $C_{18}$ column in the same manner as described above to give 9 mg of pure stalobacin E.

Fractions 91–134 (1250 mg) obtained in the first purification step were treated in the same manner as above to give pure stalobacins A (83 mg), C (2 mg), D (3 mg), F (19 mg) and G (12 mg).

EXAMPLE 2

Preparation of DNP-stalobacins A and B: A mixture of stalobacins A and B (203 mg) was dissolved in 20 ml of 50% aqueous methanol, mixed with 800 mg of sodium bicarbonate and 4 ml of 10% ethanolic solution of 2,4-dinitrofluorobenzene and stirred at room temperature for 2 hours. The reaction mixture was adjusted to pH 3.0 with dilute hydrochloric acid, and the aqueous layer was washed with ether and ethyl acetate successively and extracted with n-butanol. The organic layer was dried over sodium sulfate and concentrated in vacuo. The residue (240 mg) was subjected to high performance liquid chromatography to give 65 mg of DNP-stalobacin A (reaction product of 2,4-dinitrofluorobenzene and stalobacin A)($t_R$ 18 min.) and 29 mg of DNP-stalobacin B ($t_R$ 20.2 min.).

Separation condition:

Column = Develosil ODS 2.0 × 25 cm
Eluent = 44% acetonitrile — 2 mM phosphate buffer
(pH 7.5, containing 50 mM $Na_2SO_4$)
DNP-stalobacin A:   m.p. >230° C.
  HR-LSIMS ($MH^+$) 1649.7378
  $C_{67}H_{109}N_{16}O_{32}$ Theoretical Value 1649.7386
DNP-stalobacin B:   m.p. >230° C.
  HR-LSIMS ($MH^+$) 1530.7169
  $C_{64}H_{104}N_{15}O_{28}$ Theoretical Value 1530.7169

Physico-chemical properties of stalobacins A, B, C, D, E, F, G, DNP-stalobacin A and DNP-stalobacin B obtained in Examples 1–2 were as shown in Tables 1, 2 and 3. IR spectra of stalobacins A–G were shown in FIGS. 1–7, and NMR spectra of DNP-stalobacin A, DNP-stalobacin B, stalobacin E, stalobacin F and stalobacin G were shown in FIGS. 8–12 of the accomanying drawings, respectively. Putative partial structures of DNP-stalobacin A and DNP-stalobacin B were shown below.

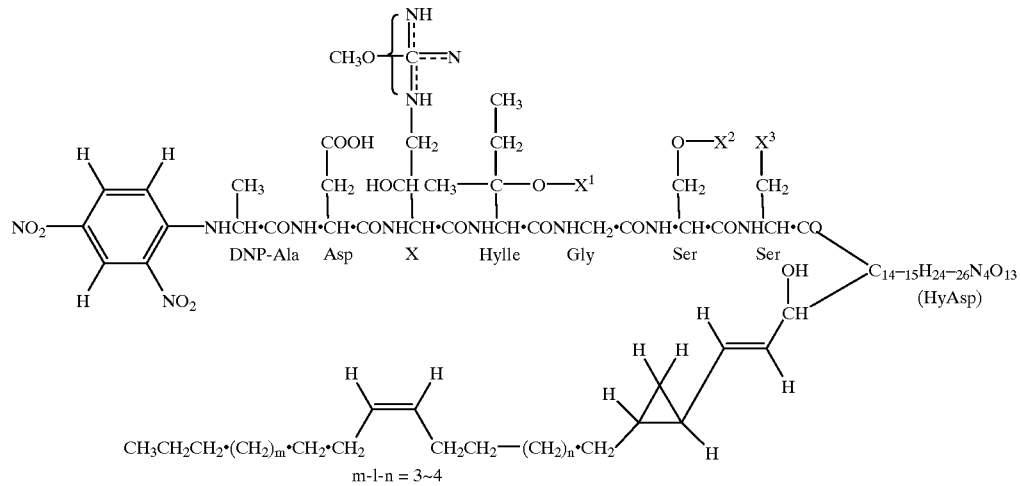

DNP-Stalobasin B

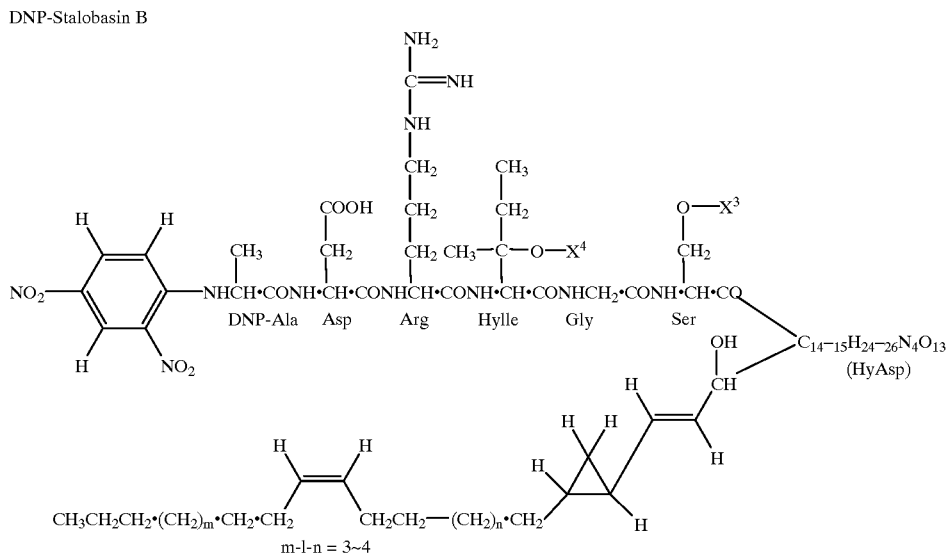

In the chemical structures above, HyAsp and HyIle represent hydroxyaspartic acid and hydroxyisoleucine, respectively, and (HyAsp) represents a moiety including hydroxyaspartic acid, and $X^1$, $X^2$, $X^3$, $X^4$ and $X^5$ represent unidentified moieties. There is possibility that all or some of $X^1$, $X^2$, $X^3$, $X^4$ and $X^5$ represent a single bond and they connect to the $C_{14-15}H_{24-25}N_4O_{13}$(HyAsp) moiety in the molecule.

Figure 13C:
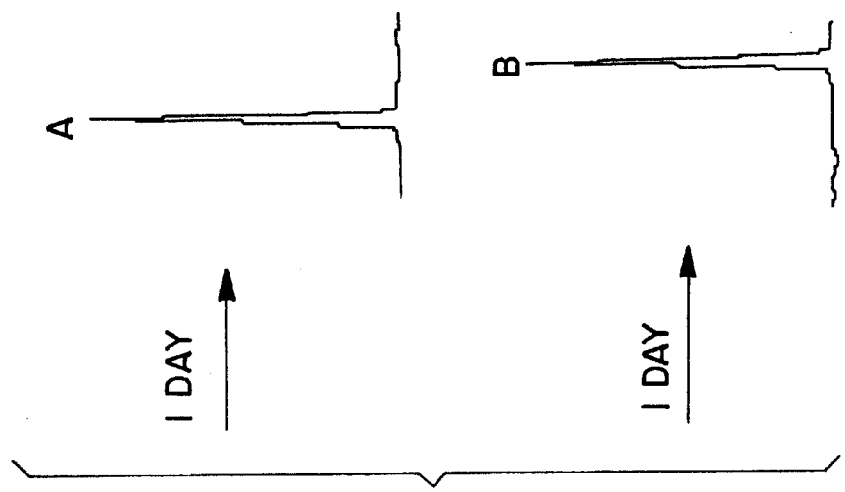
FIG. 13 shows high performance liquid chromatogram demonstrating mutual conversion between stalobacins A and A' and stalobacins B and B'.
Figure 13B:
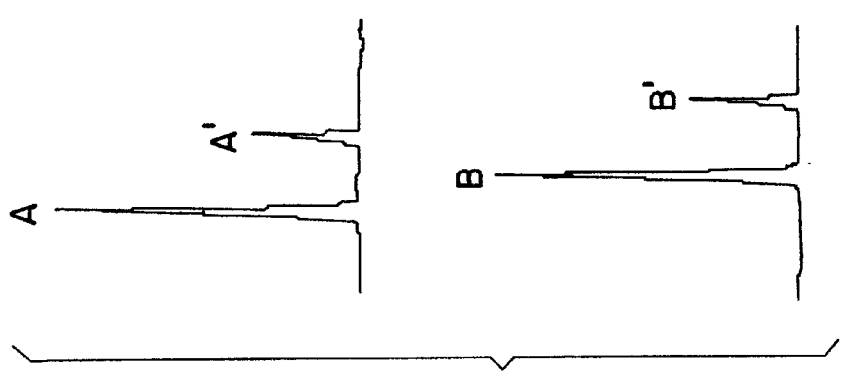
Figure 13A:
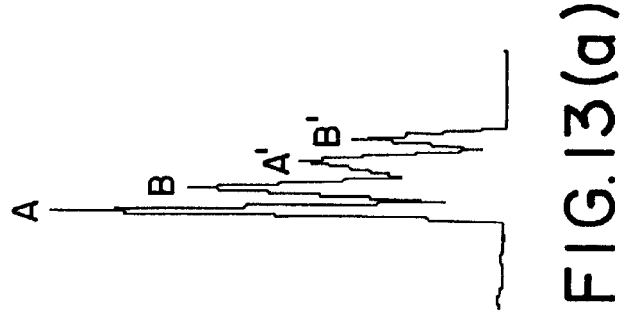

Unique Properties of Stalobacins A and B:

(1) As shown in FIG. 13(a), a mixture of stalobacins A and B was subjected to high performance liquid chromatography, whereby total 4 peaks corresponding to A, its isomer A', B and its isomer B' were observed. However, when this mixture was allowed to stand for 24 hours and then subjected again to high performance liquid chromatography, only two peaks corresponding to A and B were observed with disappearance of peaks of A' and B'. Each of A and B was isolated and again subjected to liquid chromatography, whereby two peaks corresponding to A and A' were observed for A and two peaks corresponding B and B' were observed for B (FIG. 13(b)). Each of these fractions was allowed to stand for one day, whereby the peaks of A' and B' disappeared again (FIG. 13(c)).

(2) Stalobacin B has a molecular formula $C_{58}H_{101}N_{13}O_{24}$ an IR absorption at 1747 cm$^{-1}$. It is treated with dilute NaOH to give a compound of molecular formula $C_{58}H_{103}N_{13}O_{25}$. The antibacterial activity markedly lowered with the disappearance of the absorption at 1747 cm$^{-1}$.

(3) Table 6 shows the aspect of the mutual conversion between A and A', when stalobacin A was dissolved in aqueous solution of various pH.

TABLE 6

| Time after dissolution | Composition (%)* | | | | | |
|---|---|---|---|---|---|---|
| | pH 3.0 | | pH 7.0 | | pH 8.0 | |
| | A | A' | A | A' | A | A' |
| 0 | 82.2 | 17.8 | 81.9 | 18.1 | 82.1 | 17.9 |
| 1 hour | 96.0 | 3.1 | 87.9 | 12.1 | 87.3 | 12.7 |
| 2 hour | 100 | 0 | 100 | 0 | 100 | 0 |
| 3 hour | 100 | 0 | 100 | 0 | 100 | 0 |

*: High Performance Liquid Chromatography

EXAMPLE 3

(a) Fermentation Step:

Eight hundreds ml of a medium (adjusted to pH 7 with 2N-NaOH) consisting of 1.0% glucose, 0.5% yeast extract (Difco) and tap water in a 2 L Erlenmeyer flask was inoculated with a seed strain of Pseudomonas sp. PBJ-5360-STR-1-21 (kept at —80° C. in a 2 ml vial), and the resultant mixture was subjected to a shaking cultivation at 180 rpm with 70 mm of shaking breadth at 28° C. for 22 hours. The culture (800 ml) was implanted to 20 L of a medium (adjusted to pH 7 with 2N-NaOH) containing 1.0% glucose, 0.4% yeast extract (Difco), 1.0% malt extract (Difco), 0.1% polypeptone (Nippon Seiyaku) and tap water in a 30 L jar fermenter, and the resultant mixture was cultivated with agitation at 200 rpm, with 14 L/min of aeration under 0.35 kg/cm$^2$ of inner pressure, at 28° C. for 21 hours.

Then, 8 L of this culture was implanted to 125 L of a medium (adjusted to pH 7 with 2N-NaOH) consisting of 2.0% soluble starch, 2.0% powdery yeast, 1.5%β-cyclodextrin, 0.5% olive oil, 0.3% magnesium chloride·6H$_2$O, 0.1% potassium primary phosphate, 0.0008% defoaming agent ADECANOL (Asahi Denka Kogyo) LG109 and tap water in a 250 L tank, and the resultant mixture was cultivated with 65 L/min of aeration, under 0.35 kg/cm$^2$ of inner pressure, with agitation at 350 rpm at 28° C. for 72 hours.

(b) Separation Step:

To 138 L of the culture obtained in the foregoing step was added 1.4 L of chloroform for sterilization. Then, 15 L of Amberlite XAD-7 (Organo) was added and the resulting mixture was mixed with stirring for 3 hours for a batch adsorption of the active substances onto the resin. The resin was recovered using a 0.1 mm mesh stainless steel filter. The resin was washed with water, put in a glass column (inner diameter: 20 cm), washed with 40 L of water, 40 L of 30% methanol and then 15 L of 50% methanol in 20 mM phosphate buffer (pH 7.5), and the active substances were eluted by 40 L of 60% methanol in 20 mM phosphate buffer (pH 7.5).

Fractions (20 L) showing antibacterial activity to *S. aureus* JC-1 were collected, concentrated in vacuo to 3 L. The concentrate was washed with 3 L of ethyl acetate to remove lipophilic materials. The ethyl acetate contained in the aqueous layer was evaporated in vacuo. The active substances were adsorpted on Amberlite XAD-7 (Organo) in a 1 L column (inner diameter 6.5 cm×31 cm) and the resin was washed with 2 L of water. The elution was carried out using 2 L of 30% aqueous MeOH and 3 L of 50% aqueous MeOH. The eluted fractions were subjected to a HPLC analysis, and the fractions containing stalobacins were collected, adjusted to pH 7.0 with 2N-HCl, concentrated in vacuo and lyophilized to obtain 3890 mg of powder.

(c) Purification Step:

The First Purification Step:

One thousand and eight hundred twenty mg of the crude powder obtained in the foregoing step was dissolved in 60 ml of 20 mM phosphate buffer (pH 7.5). The solution was subjected to a preparative high-speed liquid chromatography using YMC ODS column [S-15/30$\mu$, 5.0×50 cm, eluent: acetonitrile/20 mM phosphate buffer (pH 7.5). 50 mM sodium sulfate=40/60, flow rate: 50 ml/min, UV detection; 210 nm] to obtain a fraction (2.4 L) containing stalobacins H-1 and I-1 as main ingredients. The acetonitrile in the fraction was distilled off and the residue was passed through a column of Diaion HP-20 (Mitsubishi Kasei Corporation). The resin was washed with water, and the adsorbed components were eluted with 60% aqueous acetone. The acetone in the eluate was distilled away in vacuo and the residue was lyophilized to obtain 126 mg of powder.

The Second Purification Step:

The powder obtained in the above step was purified by preparative high-speed liquid chromatography under the following conditions to obtain stalobacins H-1 and I-1.

The powder (126 mg) was dissolved in 7 ml of 50 mM phosphate buffer (pH 7.0). Fifteen mg of the sample per one procedure was charged into Asahipak ODP-90 column (inner diameter 21.5 mm×300 mm, eluent: acetonitrile solution of 20 mM AcOH/aqueous solution of 20 mM AcOH= 40/60, flow rate: 8 ml/min, UV detection: 220 nm), and stalobacin H-1 was collected from the fractions of 144 ml to 184 ml and stalobacin I-1 was collected from the fractions of 216 ml to 288 ml. This fractionation was repeated, and collected fractions were neutralized to pH 7.0 with aqueous 1N-NaOH. The acetonitrile was distilled off in vacuo and NaCl was added to the residue to obtain 5% NaCl concentration. The resultant mixture was adjusted to pH 7.5 with 1N NaOH and passed through MCI GEL CHP20P column (75 to 150 $\mu$, Mitsubishi Kasei) which had been equilibrated with 5% aqueous NaCl solution. The column was washed with water and eluted with 70% aqueous MeOH. The MeOH in the eluate was distilled off in vacuo and the residue was lyophilized to give 12 mg of pure stalobacin H-1 and 38 mg of pure stalobacin I-1.

Figure 14:
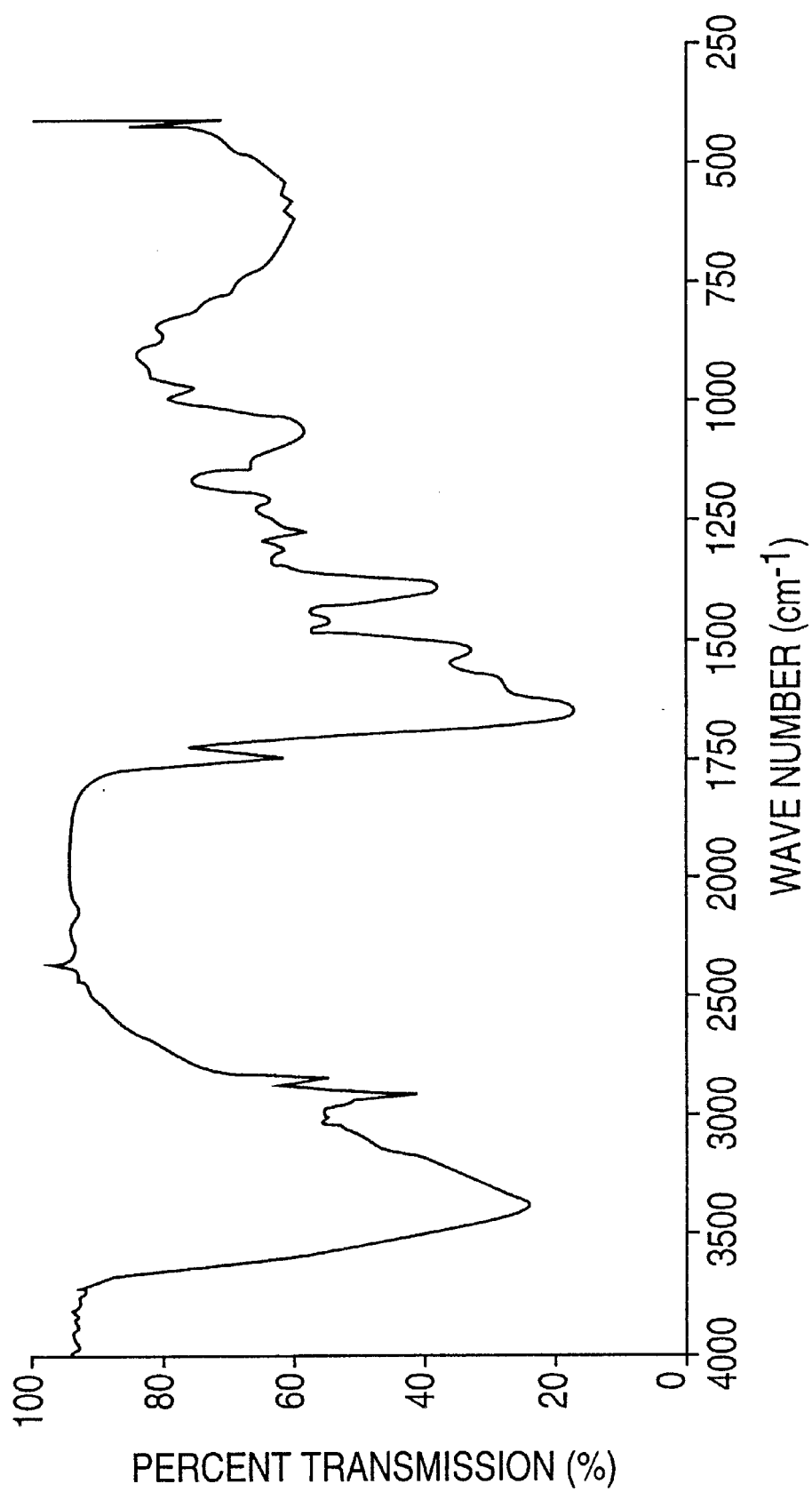
FIG. 14 is a graph showing IR spectrum of stalobacin H-1.
Figure 15:
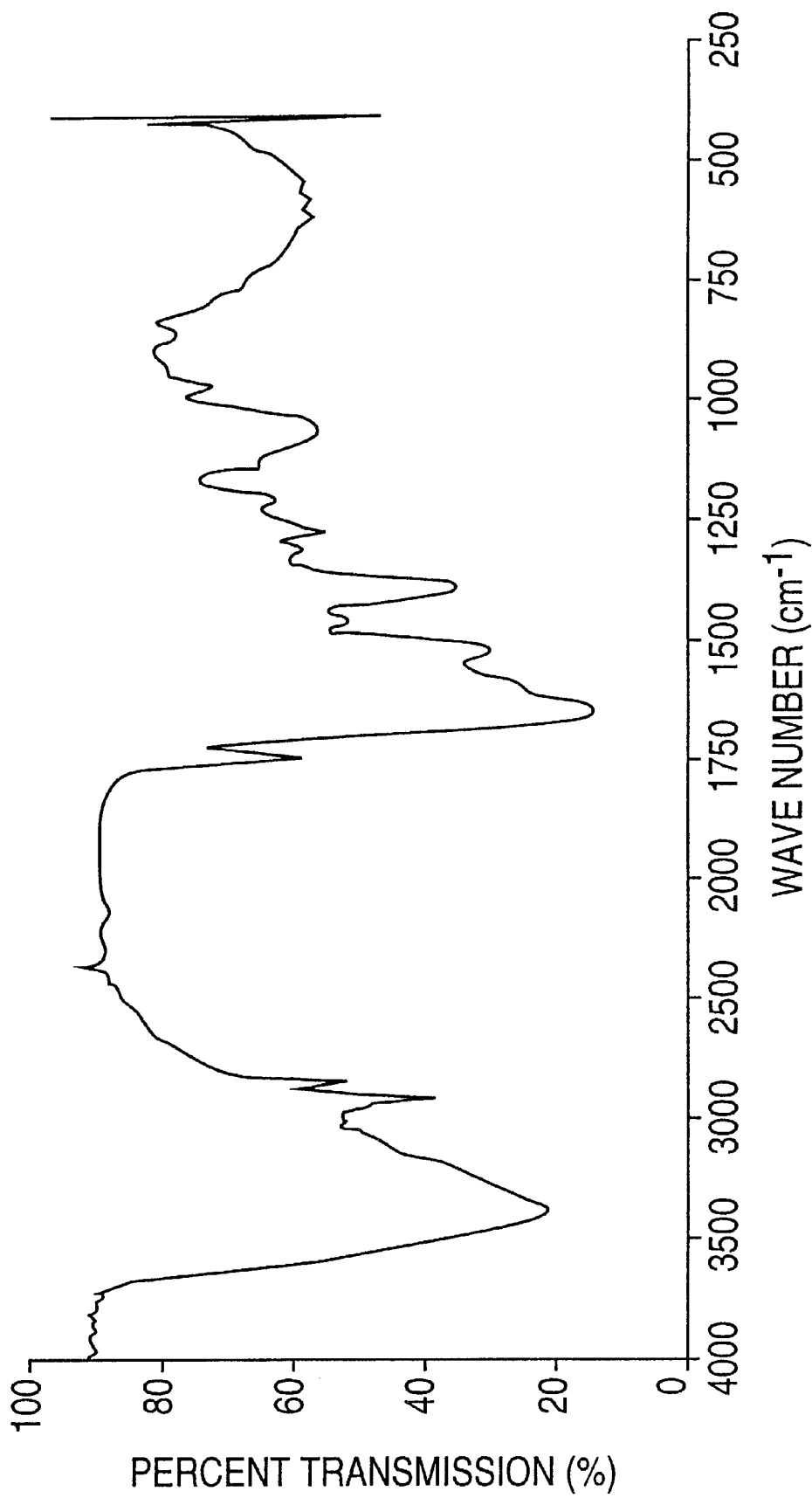
FIG. 15 is a graph showing IR spectrum of stalobacin I-1.
Figure 16:
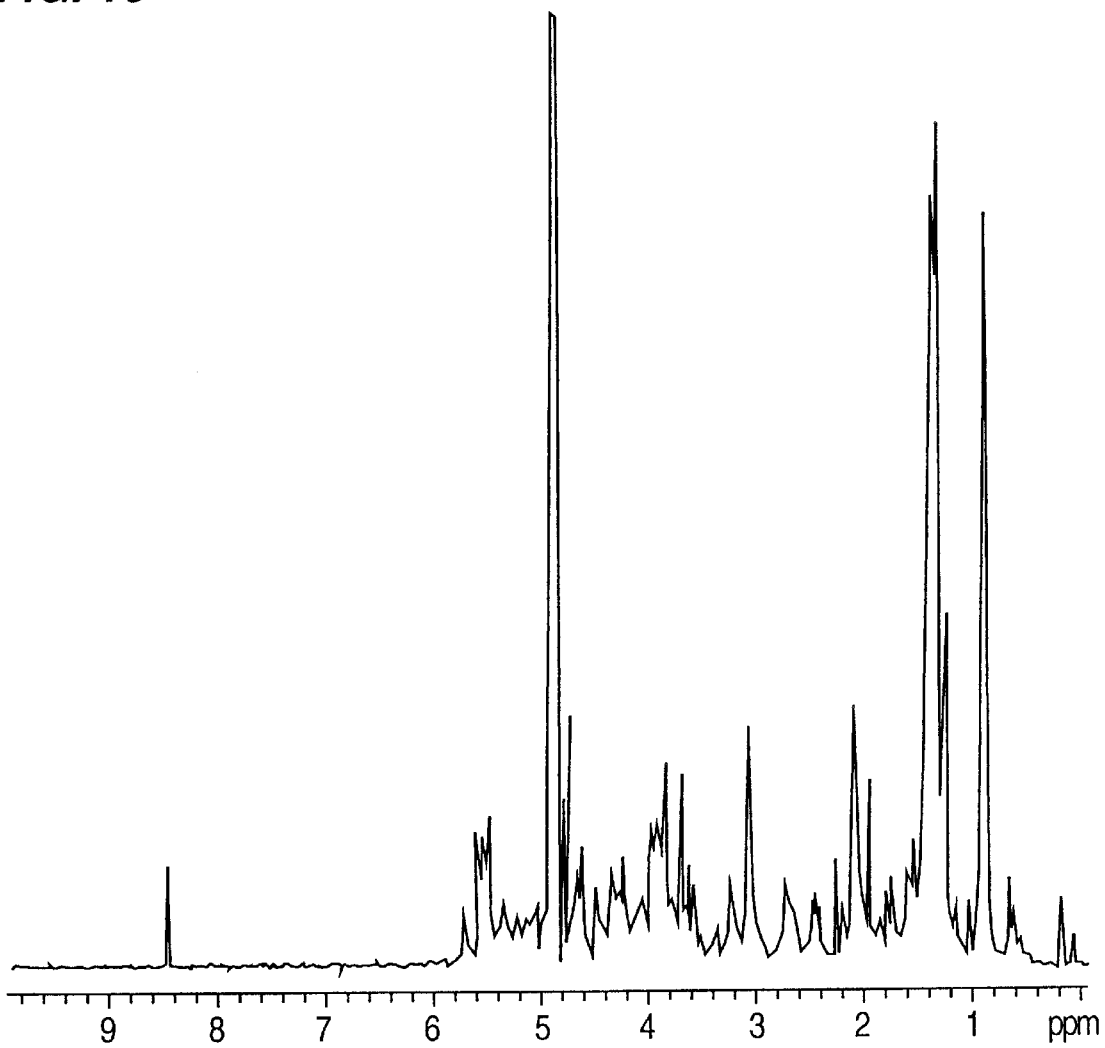
FIG. 16 is a graph showing NMR spectrum of stalobacin H-1.
Figure 17:
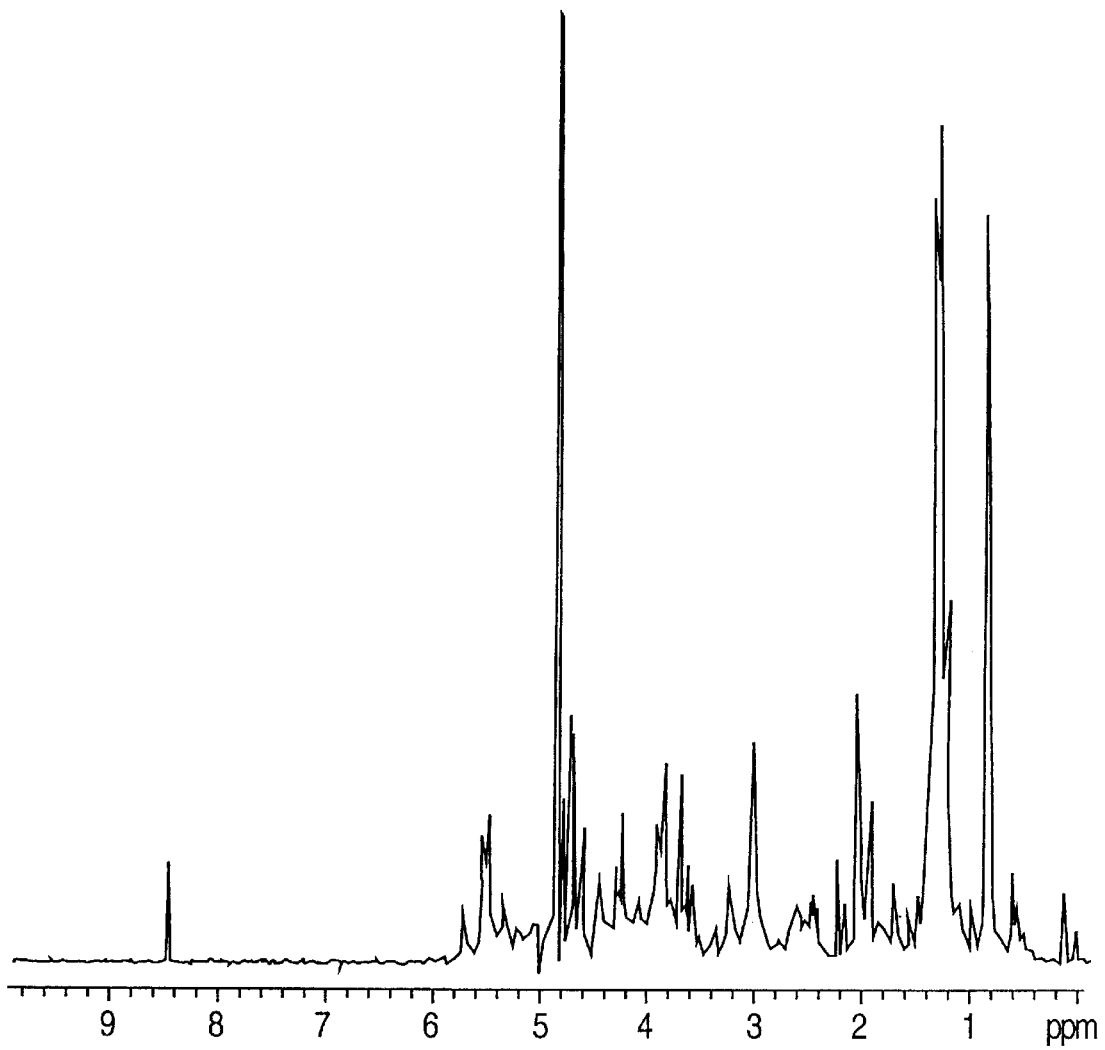
FIG. 17 is a graph showing NMR spectrum of stalobacin I-1.

Physico-chemical properties of stalobacins H-1 and I-1 obtained in Example 3 are shown in Table 9. IR spectra of stalobacins H-1 and I-1 were shown in FIGS. 14 and 15 respectively, and NMR spectra of stalobacins H-1 and I-1 were shown in FIGS. 16 and 17 respectively.

Experiment 1 Antibacterial Activity in vitro and in vivo:

1) In vitro Antibacterial Activity:

Antibacterial activity in vitro of antibiotic stalobacins A–G obtained in Example 1 was assayed by the agar dilution method. Table 7 shows the results.

TABLE 7

| Gram-positive bacteria | Stalobacin ($\mu$g/ml, $10^6$ cfu/ml) | | | | | | |
|---|---|---|---|---|---|---|---|
| | A | B | C | D | E | F | G |
| S. aureus FDA JC-1 | 0.025 | 0.1 | 0.08 | 0.01 | 0.025 | 0.02 | 0.1 |
| S. faecalis SR1004 | 0.1 | 0.39 | 0.31 | 0.08 | 0.39 | 0.1 | 0.2 |
| S. aureus 3626 (MRSA) | 0.05 | 0.1 | 0.16 | 0.04 | 0.025 | 0.05 | 0.2 |

2) In vivo Antibacterial Activity:

Antibacterial activity in vivo of stalobacin A was assayed. Mice were intraperitoneally challenged with infectious bacteria. One hour after the challenge, the test compound was subcutaneously administered. $ED_{50}$ value was calculated on the basis of survival ratio on 7th day after the challenge. MIC was determined according to the agar dilution method. Table 8 shows the results.

TABLE 8

| Protective Effect of Stalobacin A in Mice Systemically Infected | | |
|---|---|---|
| | $ED_{50}$ (mg/kg) Stalobacin A | MIC ($\mu$g/ml) Stalobacin A |
| S. aureus Smith | 0.17 | 0.006 |
| S. aureus SR3637 (H-MRSA) | 0.27 | 0.025 |
| S. pyogenes C-203 | 0.12 | 0.013 |
| S. pneumoniae Type I | 0.058 | 0.006 |

Experiment 2 Bacteriological Properties of PBJ-5,360:

Bacteriological properties of PBJ-5,360 of the present invention are shown below. PBJ-5,360 was isolated from the soil collected in Kyoto, Japan.

Cultivation was effected at 28° C. in principle.

A. Morphology:

It is a Gram-negative rod. Its size is 0.3–0.5 ($\mu$)×0.8–1.3 ($\mu$). It vigorously moves with one or more polar flagella.

B. Characteristics of Culture

1) Cultivation in Meat Infusion Medium:

Growth of the bacteria was hardly observed. Off white translucent precipitates formed very slightly at the bottom of the test tube.

2) Meat Infusion Agar Stab Culture:

Growth in thread form or small nipple form along the stab line was observed. Neither evolution of gas nor production of pigment was observed. Reddish thin bacterial plaque appeared on the surface, but this bacterial plaque became translucent and light brown with the lapse of time and verrucose projections were observed in several places. It is an aerobic bacterium.

3) Meat Infusion Agar Slant Culture:

The growth of the bacteria was not so rapid and began at 28° C. after two days (observed with naked eyes). The bacteria grew in thread form, and the bacterial plaque was translucent and light yellow with flat swelling having a spotty appearance. The periphery was whole peripheral. Then, the bacterial plaque grew favorably in thread form or verrucose form with gloss. Thus, a wet slightly reddish translucent brown bacterial plaque was obtained. The periphery was wavy or long wavy. Production of any gas or pigment was not observed.

4) Meat Infusion Gelatin Stab Culture.

Cultivation was effected at room temperature (22–25° C.). The gelatin was liquefied.

5) Cultivation on the meat infusion agar plane medium:

The growth of the bacteria was not so rapid. The colony became visible at 28° C. after two days. The colony was initially small, spotty, translucent and brown with a whole periphery. The colony was too small to be observed about its swelling. Then, the colony grew in a spotty or circular form and with whole periphery and the swelling was flat or convex circular. The colony was translucent and brown with gloss. Neither gas nor soluble pigment was produced.

6) Characteristics in Litmus Milk Culture:

An acid formation and peptonization occurred, but the reactions occurred rather slowly. Thus, the reaction began after 14 days. No gas evolved. Sometimes grey reddish purple thin pellicle formed on the surface. The upper layer was translucent and reddish purple, and the lower layer was opaque and purplish beige. The precipitate was reddish purple close to beige.

C. Physiological and Biochemical Properties:
1) Catalase test: positive
2) Oxidase test: positive
3) OF-test: negative (showing to be alkaline)
4) Hemolytic test: positive (weakly)
5) Viability at 5° C.: negative
6) Production of $H_2S$: negative
7) Reducing ability for nirate: positive
8) Denitrification: negative (although no nitrogen gas was evolved, it seemed to reduce $NO_2^-$.)
9) Availability of citric acid: negative (Christensen medium and Simons medium)
10) Growth on NAC agar medium: negative (nonviable)
11) Production of indole: negative
12) Voges-Proskauer reaction (Voges-Proskauer test): negative
13) Methylred test: negative
14) Hydrolyzing ability for arginine: positive
15) Decarboxylation ability for lysine: positive
16) Decarboxylation ability for ornithine: positive
17) Hydrolyzing ability for esculine: negative
18) DNase test: negative
19) Hydrolyzing ability for starch: negative
20) ONPG test (cultivated at 37° C.): negative
21) Acylamidase test: negative
22) Phosphatase test: positive
23) Hydrolyzing ability for chitin: negative
24) Productivity of levan from sucrose: positive
25) Productivity of acids and gas from sugars:
    Neither acids nor gases were produced from the following 13 sugars: glucose, fructose, galactose, mannose, xylose, arabinose, maltose, lactose, ramnose, sucrose, cellobiose, trehalose, mannit.
26) Accumulation of poly-β-hydroxybutyrate in the cell: negative
27) Availability of carbon sources: On the medium containing minerals, glucose and calcium 2-keto-gluconate can be used as a sole carbon source for the formation of the cells. In this case, it seemed that specific vitamines for growth were not required. On the other hand, D-(+)-trehalose, DL-arginine, geraniol, β-alanine, L-valine and innosit can not be used.
28) G+C mole % (HPLC method): 60.4% (A+T mole %=39.6%)

In view of the properties above, the present bacterium is an aerobic Gram-negative rod and moves actively in a liquid medium using one or more polar flagella. It is positive for catalase and contains oxidase. It was negative for OF-test (showing to be alkaline). In view of these observations, it is apparent that the present bacterium belongs to Genus Pseudomonas in Family Pseudomonadaceae.

When the inventors compared the above properties with those of the bacterial complexes which are incapable of accumulating poly-β-hydroxybutyrate (PHB) in their cells, which complexes are described in Bergey's Manual of Systematic Bacteriology, Vol. 1 (1984) on Genus Pseudomonas, the present inventors failed to find any bacterium having those properties consistent or analogous to the properties described above. Therefore, this bacterium may be a new strain of Pseudomonas, and it appears a considerably unusual strain of Pseudomonas because it hydrolyzes arginine and decarboxylates lysine and ornithine. The G+C mole % value of 60.4% indicates that the strain belongs to a group having lower G+C value in Pseudomonas. Thus, in view of the various properties above, the present bacterium has been designated as Pseudomonas sp. PBJ-5,360.

Experiment 3 Antibacterial Activity in vitro and in vivo

1) In vitro Antibacterial Activity:

Antibacterial activity in vitro of antibiotic stalobacins H-1 and I-1 obtained in Example 3 was assayed by the agar dilution method. The results are shown in Table 9.

TABLE 9

| Gram-positive bacteria | Stalobacin (μg/ml), $10^6$ cfu/ml) | |
|---|---|---|
| | H-1 | I-1 |
| S. aureus FDA JC-1 | 0.1 | 0.05 |
| S. faecalis SR1004 | 0.2 | 0.2 |
| S. aureus 3626 (MRSA) | 0.1 | 0.1 |

2) In vivo Antibacterial Activity:

Antibacterial activity in vivo of stalobacin I-1 was assayed. Mice were intraperitoneally challenged with infectious bacteria. One hour after the challenge, the test compound was subcutaneously administered. $ED_{50}$ values was calculated on the basis of survival ratio on 7th day after the challenge. MIC was determined according to the agar dilution method. The results are shown in Table 10.

TABLE 10

| Protective Effect of Stalobacin I-1 in Mice Systemically Infected | | |
|---|---|---|
| | $ED_{50}$ (mg/kg) Stalobacin I-1 | MIC (μg/ml) Stalobacin I-1 |
| S. aureus SR3637 (H-MRSA) | 0.12 | 0.012 |
| S. pneumoniae Type I | 0.046 | 0.006 |
| E. faecalis SR1004 | 1.50 | 0.2 |

Experiment 4 Bacteriological Properties of PBJ-5360 and PBJ-5360-STR-1-21:

PBJ-5360-STR-1-21 of the present invention was obtained as a mutant of the above-mentioned PBJ-5360 strain. PBJ-5360 was isolated from the soil collected in Kyoto, Japan. Various bacteriological properties of PBJ-5360-STR-1-21 of the present invention are shown below. Cultivation was effected at 28° C. in principle.

A. Morphology:

It is a Gram-negative rod. Its size is 0.3–0.5 (μm)×0.8–1.3 (μm). It vigorously moves with one or more polar flagella.

15

B. Characteristics of Culture

1) Cultivation in Meat Infusion Medium:

Growth of the bacteria was hardly observed. Off white translucent precipitates formed very slightly at the bottom of the test tube.

2) Meat Infusion Agar Stab Culture:

Growth in thread form or small nipple form along the stab line was observed. Neither evolution of gas nor production of pigment was observed. Reddish thin bacterial plaque appeared on the surface, but this bacterial plaque became translucent and light brown with the lapse of time and verrucose projections were observed in several places. It is an aerobic bacterium.

3) Meat Infusion Agar Slant Culture:

The growth of the bacteria was not so rapid and began at 28° C. after two days (observed with naked eyes). The bacteria grew in thread form, and its bacterial plaque was translucent and light yellow with flat swelling having spotty appearance. The periphery was whole peripheral. Then, the bacterial plaque grew favorably in thread form or verrucose form with gloss. Thus, a wet slightly reddished translucent brown bacterial plaque was obtained. The periphery was wavy or long wavy. Production of any gas or pigment was not observed.

4) Meat Infusion Gelatin Stab Culture:

Cultivation was effected at room temperature (22–25° C.). The gelatin was slightly liquefied.

5) Cultivation on the Meat Infusion Agar Plane Medium:

The growth of the bacteria was not so rapid. The colony became visible at 28° C. after two days. The colony was initially small, spotty, translucent and brown with a whole periphery. The colony was two small to be observed about its swelling. Then, the colony grew in a spotty or circular form and with whole periphery and the swelling was flat or convex circular. The colony was translucent and brown with gloss. Neither gas nor soluble pigment was produced.

6) Characteristics in Litmus Milk Culture:

An acid formation did not occur, and peptonization occurred but the reaction began after 14 days. Thus, the reaction was rather slowly. No gas evolved.

C. Physiological and Biochemical Properties

1) Catalase test: positive
2) Oxidase test: positive
3) OF-test: negative (showing to be alkaline)
4) Hemolytic test: positive (weakly)
5) Viability at 5° C.: negative
6) Production of $H_2S$: negative
7) Reducing ability for nitrate: positive
8) Denitrification: negative (although no nitrogen gas was evolved, it seemed to reduce $No_2^-$)
9) Availability of citric acid: negative (Christensen medium and Simons medium)
10) Growth on NAC agar medium: negative (nonviable)
11) Production of indole: negative
12) Voges-Proskauer reaction (Voges-Proskauer test): negative
13) Methyl Red test: negative
14) Hydrolyzing ability for arginine: weakly positive
15) Decarboxylation ability for lysine: positive
16) Decarboxylation ability for ornithine: positive
17) Hydrolyzing ability for esculin: negative
18) DNase test: negative
19) Hydrolyzing ability for starch: negative
20) ONPG test (cultivated at 37° C.): negative
21) Acylamidase test: positive
22) Phosphatase test: positive
23) Hydrolyzing ability for chitin: negative

16

24) Productivity of levan from sucrose: positive
25) Productivity of acids and gas from sugars: Neither acids nor gases were produced from the following 13 sugars: glucose, fructose, galactose, mannose, xylose, arabinose, maltose, lactose, rhamnose, sucrose, cellobiose, trehalose and mannitol.
26) Accumulation of poly-β-hydroxybutyrate in the cell: negative
27) Availability of carbon sources: On the medium containing minerals, glucose and calcium 2-keto-gluconate can be used as a sole carbon source for the formation of the cells. In this case, it seemed that specific vitamins for growth were not required. On the other hand, D-(+)-trehalose, DL-arginine, geraniol, β-alanine, L-valine and inositol were not be utilized.
28) G+C mole % (HPLC method): 60.4% (A+T mole % =39.6%)

In view of the above test results, PBJ-5360-STR-1-21 is an aerobic Gram-negative rod and moves actively in a liquid medium using one or more polar flagella. It is positive for catalase and contains oxidase. It was negative for OF-test (showing to be alkaline). In view of these observations, it is apparent that the present bacterium belongs to Genus Pseudomonas in Family Pseudomonadaceae.

When the inventors compared the above properties with those of the bacterial complexes which are incapable of accumulating poly-β-hydroxybutyrate (PHB) in their cells, which complexes are described in Bergey's Manual of Systematic Bacteriology, Vol. 1 (1984) on Genus Pseudomonas, the present inventors failed to find any bacterium having those properties consistent or analogous to the properties described above. This bacterium appears a considerably unusual strain of Pseudomonas because it hydrolyzes arginine and decarboxylates lysine and ornithine. The G+C mole % value of 60.4% indicates that the strain belongs to a group having lower G+C value in Pseudomonas. Thus, in view of the various properties mentioned above, the present bacterium has been identified as Pseudomonas sp. PBJ-5360-STR-1-21. These properties were consistent with those of the parent strain PBJ-5360.

What is claimed is:

1. Antibiotic stalobacin selected from the group consisting of stalobacins H-1 and I-1 having physico-chemical properties as shown below:

|  | Stalobacin H-1 | Stalobacin I-1 |
|---|---|---|
| m.p. (° C.) (as Na salt) | 235° C. (dec.) | 240° C. (dec.) |
| LSI-MS Maximal Peak (m/z) | 1396 | 1325 |
| HRLSI-MS (MH$^+$)(m/z) | 1396.6985 | 1325.6583 |
|  | $C_{60}H_{97}N_{15}O_{23}$ | $C_{57}H_{92}N_{14}O_{22}$ |
| Theoretical value | 1396.6954 | 1325.6583 |
| IR (KBr) (cm$^{-1}$) | 3374, 1747, 1654, 1597, 1525 | 3387, 1747 1651, 1596, 1527 |
| UV ($H_2O$) | Terminal absorption | Terminal absorption |
| CD ($H_2O$) | $[\theta]_{194} - 66980$ |  |
|  | $[\theta]_{212} + 9851$ | $[\theta]_{206} + 11530$ |
|  | $[\theta]_{232} - 31520$ | $[\theta]_{232} - 28660$ |
|  | $[\theta]_{257} + 4288$ | $[\theta]_{257} + 4749$ |
| Retention time (min.) in HPLC* | 8.8 | 9.7 |
| Amino Acid Analysis (molar ratio) |  |  |
| HyAsp[1] | HyAsp (1) | HyAsp (1) |
| Asp | Asp (1) | Asp (1) |
| Ser | Ser (1) | Ser (1) |
| HyIle[2] | HyIle (1) | HyIle (1) |

-continued

|  | Stalobacin H-1 | Stalobacin I-1 |
|---|---|---|
| Gly | Gly (1) | Gly (1) |
| Ala | Ala (1) | — |

*Column: Develosil 5C18, 4.6 i.d. × 250 mm
Mobile phase: $CH_3CN$/2 mM $H_3PO_4$ (containing 50 mM $Na_2SO_4$) = 43/57
Flow rate: 1 ml/min.
[1]Hydroxyaspartic acid
[2]Hydroxyisoleucine.

2. Pseudomonas sp. PBJ-5360-STR-1-21 deposited under accession no. FERM BP-4661 which produces an antibiotic stalobacin as described in claim 1.

3. A process for producing an antibiotic stalobacin as defined in claim 1, which comprises cultivating Pseudomonas sp. PBJ-5360-STR-1-21 deposited under accession no. FERM BP-4661 which produces an antibiotic stalobacin as described in claim 1 and separating and recovering the antibiotic stalobacin from the culture.

* * * * *